United States Patent
Freid et al.

(10) Patent No.: US 7,303,564 B2
(45) Date of Patent: *Dec. 4, 2007

(54) SPINAL PLATE EXTENDER SYSTEM AND METHOD

(75) Inventors: James M. Freid, Round Rock, TX (US); Erik J. Wagner, Austin, TX (US)

(73) Assignee: Spinal Concepts, Inc., Austin, TX (US)

( * ) Notice: Subject to any disclaimer, the term of this patent is extended or adjusted under 35 U.S.C. 154(b) by 298 days.

This patent is subject to a terminal disclaimer.

(21) Appl. No.: 10/356,391

(22) Filed: Jan. 31, 2003

(65) Prior Publication Data

US 2003/0225409 A1    Dec. 4, 2003

Related U.S. Application Data

(60) Provisional application No. 60/353,331, filed on Feb. 1, 2002.

(51) Int. Cl.
 *A61B 17/56* (2006.01)
 *A61F 2/30* (2006.01)

(52) U.S. Cl. ...................................................... 606/69

(58) Field of Classification Search ............. 606/69–73
See application file for complete search history.

(56) References Cited

U.S. PATENT DOCUMENTS

| | | | | |
|---|---|---|---|---|
| 2,406,832 A | * | 9/1946 | Hardinge | 606/71 |
| 2,486,303 A | * | 10/1949 | Longfellow | 606/71 |
| 3,547,114 A | * | 12/1970 | Haboush | 606/71 |
| 3,604,414 A | * | 9/1971 | Borges | 606/105 |
| 4,388,921 A | | 6/1983 | Sutter et al. | |
| 4,973,332 A | * | 11/1990 | Kummer | 606/65 |
| 5,053,036 A | | 10/1991 | Perren et al. | |
| 5,470,333 A | * | 11/1995 | Ray | 606/61 |
| 5,484,439 A | * | 1/1996 | Olson et al. | 606/65 |
| 5,607,428 A | | 3/1997 | Lin | |
| 5,735,853 A | | 4/1998 | Olerud | |
| 5,876,402 A | | 3/1999 | Errico et al. | |
| 6,017,345 A | | 1/2000 | Richelsoph | |
| 6,030,389 A | | 2/2000 | Wagner et al. | |
| 6,193,721 B1 | | 2/2000 | Michelson | |
| 6,235,033 B1 | * | 5/2001 | Brace et al. | 606/69 |
| 6,306,136 B1 | * | 10/2001 | Baccelli | 606/61 |
| 6,331,179 B1 | | 12/2001 | Freid et al. | |
| 6,406,478 B1 | * | 6/2002 | Kuo | 606/71 |
| 6,454,769 B2 | | 9/2002 | Wagner et al. | |
| 6,602,256 B1 | * | 8/2003 | Hayes | 606/69 |
| 6,645,208 B2 | * | 11/2003 | Apfelbaum et al. | 606/61 |
| 6,872,210 B2 | * | 3/2005 | Hearn | 606/69 |
| 7,112,202 B2 | * | 9/2006 | Michelson | 606/71 |

* cited by examiner

*Primary Examiner*—Anuradha Ramana
(74) *Attorney, Agent, or Firm*—Michael Woods; Beth A. Vrioni

(57) ABSTRACT

A bone plate system is provided which maintains intervertebral spacing and stability of a spine. In an embodiment, a bone plate system may include a base plate with an opening through which the fastener may be positioned to allow the fastener to be inserted into a human bone at a desired angle relative to the plate. Some embodiments of a bone plate system may include a base plate and an extender plate. An extender plate may be coupled to a base plate while the base plate is coupled to the bone.

16 Claims, 19 Drawing Sheets

SPINAL PLATE EXTENDER SYSTEM AND METHOD

PRIORITY CLAIM

This application claims priority to Provisional Patent Application No. 60/353,331 entitled "SPINAL PLATE SYSTEM FOR STABILIZING A PORTION OF A SPINE" filed on Feb. 1, 2002.

BACKGROUND

1. Field of the Invention

The present invention generally relates to bone fixation systems. An embodiment of the invention relates to an extender plate that attaches to a previously inserted bone plate. The extender plate may allow for stabilization of an additional vertebral level or levels.

2. Description of Related Art

An intervertebral disc may be subject to degeneration caused by trauma, disease, and/or aging. The intervertebral disc that becomes degenerated may have to be partially or fully removed from a spinal column. Partial or full removal of the intervertebral disc may destabilize the spinal column. Destabilization of a spinal column may result in alteration of a natural separation distance between adjacent vertebrae. Maintaining the natural separation between vertebrae helps to prevent pressure from being applied to nerves that pass between vertebral bodies. Excessive pressure applied to the nerves may cause pain and/or nerve damage. During a spinal fixation procedure, a spinal implant may be inserted in a space created by the removal or partial removal of an intervertebral disc between adjacent vertebrae. The spinal implant may maintain the height of the spine and restore stability to the spine. Intervertebral bone growth may fuse the spinal implant to adjacent vertebrae.

A spinal implant may be inserted during a spinal fixation procedure using an anterior, lateral, or posterior spinal approach. In some situations, an anterior approach may result in an easier approach, less muscle and tissue damage, and/or less bone removal than other approaches.

A discectomy may be performed to remove or partially remove a defective or damaged intervertebral disc. The discectomy creates a disc space for a spinal implant. After a discectomy, the spinal implant may be inserted into the disc space. One or more spinal implants may be inserted between a pair of vertebrae. Spinal implants may be inserted into disc spaces prepared at multiple vertebral levels during a spinal fusion procedure.

A spinal plate may be coupled to vertebrae after insertion of the spinal implant. The spinal plate may stabilize the vertebrae and inhibit backout of the spinal implant from between vertebrae. A spinal plate may share a compressive load applied to the spinal implant or spinal implants inserted between vertebrae. Fasteners (e.g., bone screws) may be used to fasten the spinal plate to vertebrae. Spinal plates may be used to stabilize sections of cervical spine and/or sections of lumbar spine.

Fastening systems used to attach a spinal plate to vertebrae may attach the spinal plate to the vertebrae without allowing fasteners of the fastening systems to backout from the vertebrae. A fastening system may include a fastener and a ring. The ring may be positioned between the plate and the fastener. Backout of fasteners from the spinal plate may be inhibited without allowing the fasteners or the rings to immovably fix to the spinal plate. The ability to fasten the plate to the vertebrae without the fastening system immovably fixing to the plate may allow the position of the plate relative to the screws to change to accommodate for settling of the vertebrae. U.S. Pat. No. 6,331,179 to Freid et al. and U.S. Pat. No. 6,454,769 to Wagner et al., both of which are incorporated by reference as if fully set forth herein, describe bone plate systems.

SUMMARY

A bone plate system may be used to stabilize vertebrae. In some embodiments, a bone plate system may include a bone plate that is relatively thin (i.e., the plate has a small height). The thin bone plate may have a low profile when coupled to vertebra. The thin bone plate may include mounts that allow an extender plate to be attached to the bone plate should a need arise to stabilize an additional vertebral level or levels adjacent to the vertebral level or levels stabilized by the bone plate.

A bone plate of a bone plate system may be available in various sizes. The size of a bone plate used for a patient may depend on the number of vertebrae to be stabilized and/or size of the patient. The bone plate may include mounts that allow an extender plate or extender plates to be attached to the bone plate. In an embodiment, the mounts include openings that accept protrusions of an extender plate. In an embodiment, the mounts include protrusions that fit in openings of the extender plate. The extender plate may include an engager or engagers that couple to the bone plate to inhibit movement of the extender plate relative to the bone plate when the bone plate mounts are coupled to the extender plate.

Bone plates and extender plates may include openings that allow fastening systems to secure a bone plate and/or an extender plate to a vertebra or vertebrae. A fastening system may include a fastener and a retainer. The fastener may secure a plate to a vertebra. The retainer may couple the fastener to the plate. The retainer may couple the fastener to the plate to inhibit backout of the fastener from the plate. The retainer may secure the fastener to the plate without the retainer becoming fixedly attached to the plate (i.e., the retainer is free to rotate relative to the plate, but removal of the retainer from the plate is inhibited). Inhibiting the fastener from fixedly attaching to the plate may allow the fastener to secure the plate against a vertebra while inhibiting the fastener from backing out of the plate.

In some bone plate embodiments, an opening may be formed in a plate so a portion of the plate has a spherical contour. The spherical contour may allow a retainer that has a mating contour to be angulated in the opening. Angulation of the retainer may allow a fastener positioned through the retainer to be oriented at a desired angle into a vertebrae. The spherical contour may inhibit inadvertent removal of a retainer positioned in the opening.

In some bone plate embodiments, an opening may include a recessed portion in a wall of the plate. A portion of a retainer may fit in the recess to inhibit inadvertent removal of the retainer from the plate. A recess may have a larger height than a height of the portion of a retainer that fits in the recess. The greater height of the recess may allow for some angulation adjustment of a fastener positioned through the retainer into a vertebra. In some opening embodiments, the opening may be formed through the plate at a bias so that a fastener inserted into the opening will be positioned at a desired angle relative to the plate.

Fasteners may be angulated relative to a plate to facilitate a secure connection of a plate to vertebrae. Some plates may include openings that allow for less angulation relative to the plate at a caudal end of the plate as compared to a cephalic end of the plate. In an embodiment, openings may allow for about 6° of angulation of a fastener relative to the plate at a caudal end of the plate. The openings in the cephalic end may be biased at about a 6° angle to allow fasteners in the cephalic end to be angulated from about 6° to about 12° relative to the plate.

Fasteners may be secured in a plate using a retainer such as a ring. Rings may be positioned in the opening between the plate and fastener. In some ring embodiments, a ring includes a gap that allows for expansion and/or contraction of the ring. The expansion and/or contraction of a ring may allow a ring to be securely coupled to a plate during use.

In an embodiment, a ring is compressed and inserted into an opening in a plate. After the ring is in the plate, compressive force applied to the ring is removed to allow the ring to expand. The shape of the opening and the shape of the ring inhibit removal of the ring from the opening. A fastener may be positioned through the ring to couple the plate to a vertebra. Coupling the ring to the plate prior to insertion of the plate into a patient may simplify a bone plate insertion procedure and inhibit misplacement or dropping of a ring during the insertion procedure.

A fastener may be positioned through a retainer and bone plate into a vertebra. In an embodiment, a portion of the head of a fastener expands a retainer during insertion of the fastener into the vertebra. When the portion passes the retainer, the ring may contract so that the retainer will inhibit backout of the fastener from the bone plate. In some embodiments, a portion of the retainer fits in a recess in the fastener head. In some embodiments, the retainer may be attached to the fastener head and expand into a recess formed in the bone plate during insertion of the fastener into the vertebra.

In some bone plate system embodiments, a bone plate may include a central opening or openings. A central opening may be located in a plate at a location between caudal openings and cephalic openings that are used to attach the bone plate to vertebrae. A central opening may be used to couple a spinal implant to a bone plate. In some embodiments, a fastener may be inserted directly into a central opening. In some embodiments, a fastening system that includes a fastener and a retainer may be inserted into a central opening.

In some embodiments, an extender plate may be coupled to a bone plate. The extender plate may be used to lengthen the portion of the spine that is stabilized. An extender plate may be attached to a bone plate should degeneration of an adjacent intervertebral disc occur after a first spinal fusion procedure. An extender plate may include an overlay section and a coupling section. The coupling section may attach to a mount or mounts of a bone plate. The extender plate may include an engagement mechanism. The engagement mechanism may contact the bone plate to inhibit movement of the extender plate relative to the engaging plate after the engagement mechanism is activated.

BRIEF DESCRIPTION OF THE DRAWINGS

Advantages of the present invention will become apparent to those skilled in the art with the benefit of the following detailed description and upon reference to the accompanying drawings in which.

Figure 1:
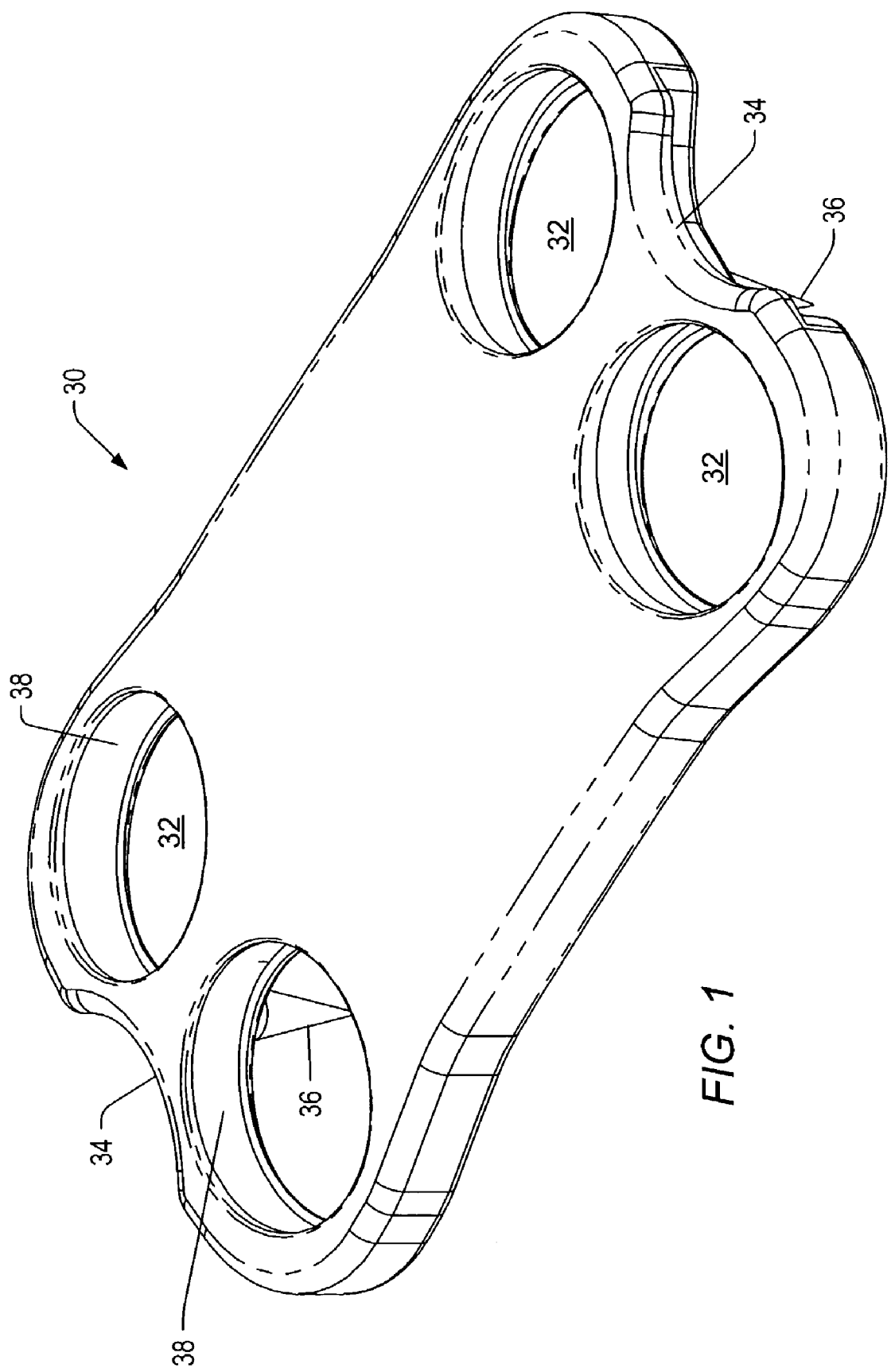
FIG. 1 depicts a perspective view of an embodiment of a base plate for a bone plate system.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF EMBODIMENTS

Bone plate systems may be used to join together bone segments and/or bones. Bone plates may be used to correct problems resulting from injury and/or disease. Bone plates may be used to join together long bones (e.g., femur, tibia, humerus, etc.). A bone plate may also be used to join together vertebra. Such a bone plate may be referred to as a spinal plate or a base plate. In some embodiments, base plates may be used to stabilize cervical vertebrae. Base plates may also be used to stabilize other types of vertebrae.

In an initial operation, a base plate may be installed in a patient. The base plate may stabilize vertebrae. A base plate may be used to stabilize one or more vertebral levels depending on the patient's needs. One vertebral level may include a first vertebra, a second vertebra adjacent to the first vertebra, and an intervertebral space between the first and second vertebrae. In some embodiments, the intervertebral space may include an intervertebral disc and/or a spinal implant. Using plates in combination with other devices (e.g., spinal implants) may ensure that the vertebral bodies are stabilized and/or that distraction between adjacent vertebral bodies is maintained. Base plates may also inhibit movement of spinal implants positioned between vertebrae.

In some situations, stabilization of vertebrae with a base plate may affect neighboring vertebral levels. Changes in neighboring vertebral levels may necessitate further stabilization of the spine. Removal of an installed base plate may be contraindicated. The installed base plate may limit options as to installing a longer plate that covers affected vertebral levels. Instead of installing a longer plate, an extender plate or extender plates may be coupled to the installed base plate to extend a region of spinal stabilization.

In some embodiments, a bone plate system may include a base plate, an extender plate, fasteners, and/or retainers. Plates in a bone plate system may include base plates and extender plates. Initially, a base plate may be coupled to vertebrae to form an initial bone plate system. At a later time, an extender plate may be coupled to the base plate to lengthen the bone plate system.

FIG. 1 depicts an embodiment of base plate 30 of a bone plate system. Base plate 30 may include openings 32, indentions 34, and spikes 36. Opening 32 may define wall 38 of base plate 30. In some embodiments, wall 38 may have a spherical contour. A diameter of opening 32 may decrease radially from about a midpoint of wall 38. In some embodiments, wall 38 of opening 32 may be surface treated or include a liner, coating, and/or covering. Surface treatment, liners, coatings, and/or coverings may be used to adjust the frictional properties and/or the wear properties of the material defining openings 32. Openings 32 may be positioned to allow bone plate 30 to attach to at least two vertebrae.

A caudal end and/or cephalic end of base plate 30 may include indention 34. In some embodiments, an end of base plate 30 may include more than one indention. Indentions 34 may facilitate connection of an extender plate to base plate 30.

A caudal end and/or cephalic end of base plate 30 may include spike 36. During manufacturing of a base plate, openings may be formed in the body of the base plate. Spikes may be securely positioned in the openings. Spikes may be, but are not limited to being, press fit, welded, glued, or otherwise affixed to the body of the base plate. In some embodiments, an end of base plate 30 may include more than one spike. Spike 36 may be driven into a vertebra to initially couple base plate 30 to the vertebra. After a base plate is initially coupled to a vertebra, the base plate may be more securely coupled to the vertebra using a fastening system. Spikes 36 may include a coating or be surface treated to promote osseointegration.

A fastening system may include a fastener and a retainer. A fastener is any elongated member that is securable in bone. A fastener may be threaded or non-threaded. Fasteners may include, but are not limited to, screws (e.g., bone screws), barbs, nails, brads, rivets, pins, spikes, and trocars. A retainer may fit in an opening of a plate between the plate and a portion of a fastener. Retainers may include, but are not limited to, rings (e.g., c-rings), one or more crescents, tabs, annuli, cinctures, liners, and gaskets.

Figure 2:
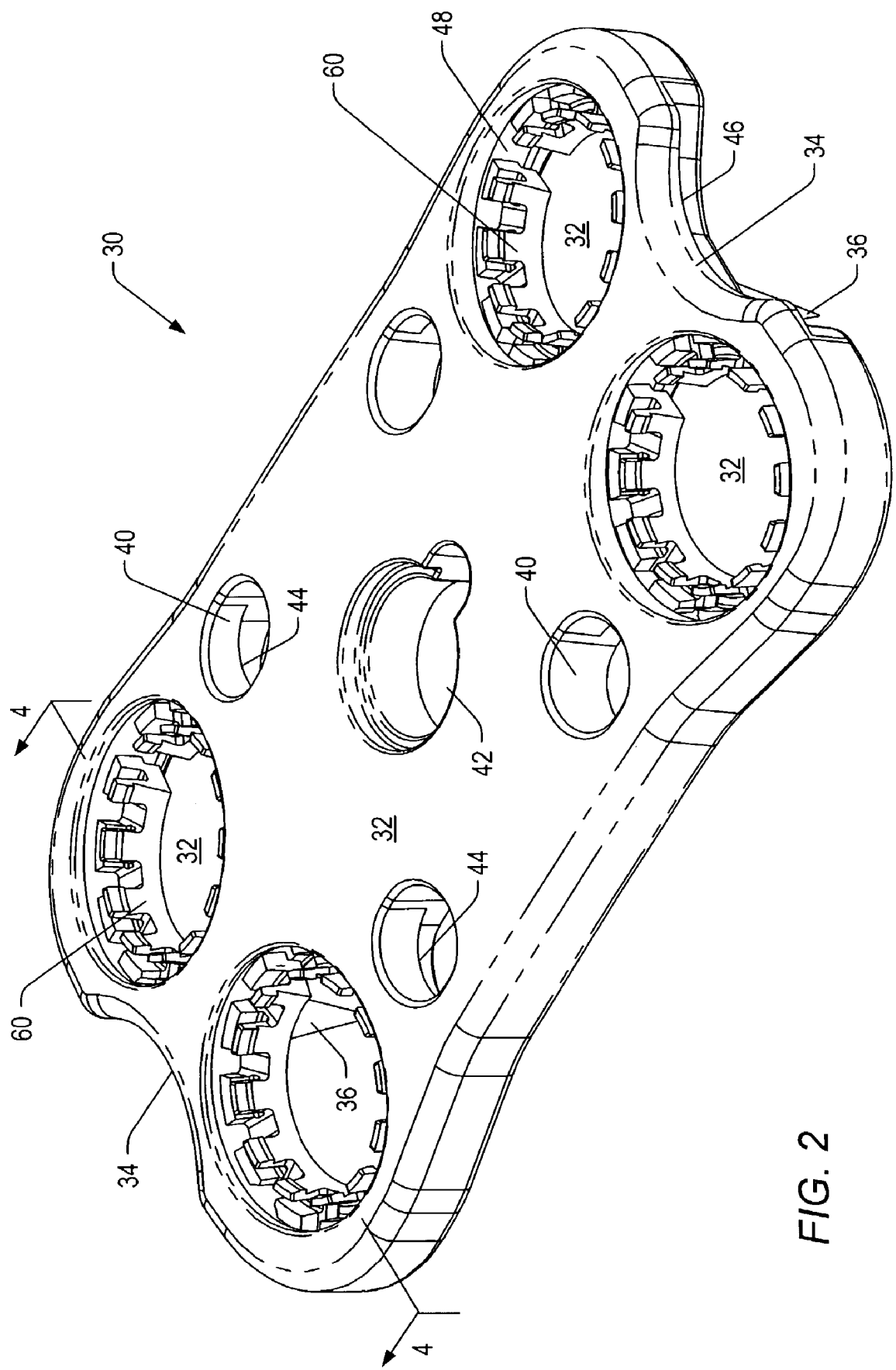
FIG. 2 depicts a perspective view that emphasizes a top of an embodiment of a base plate for a bone plate system with retainers positioned in openings of the base plate.
Figure 3:
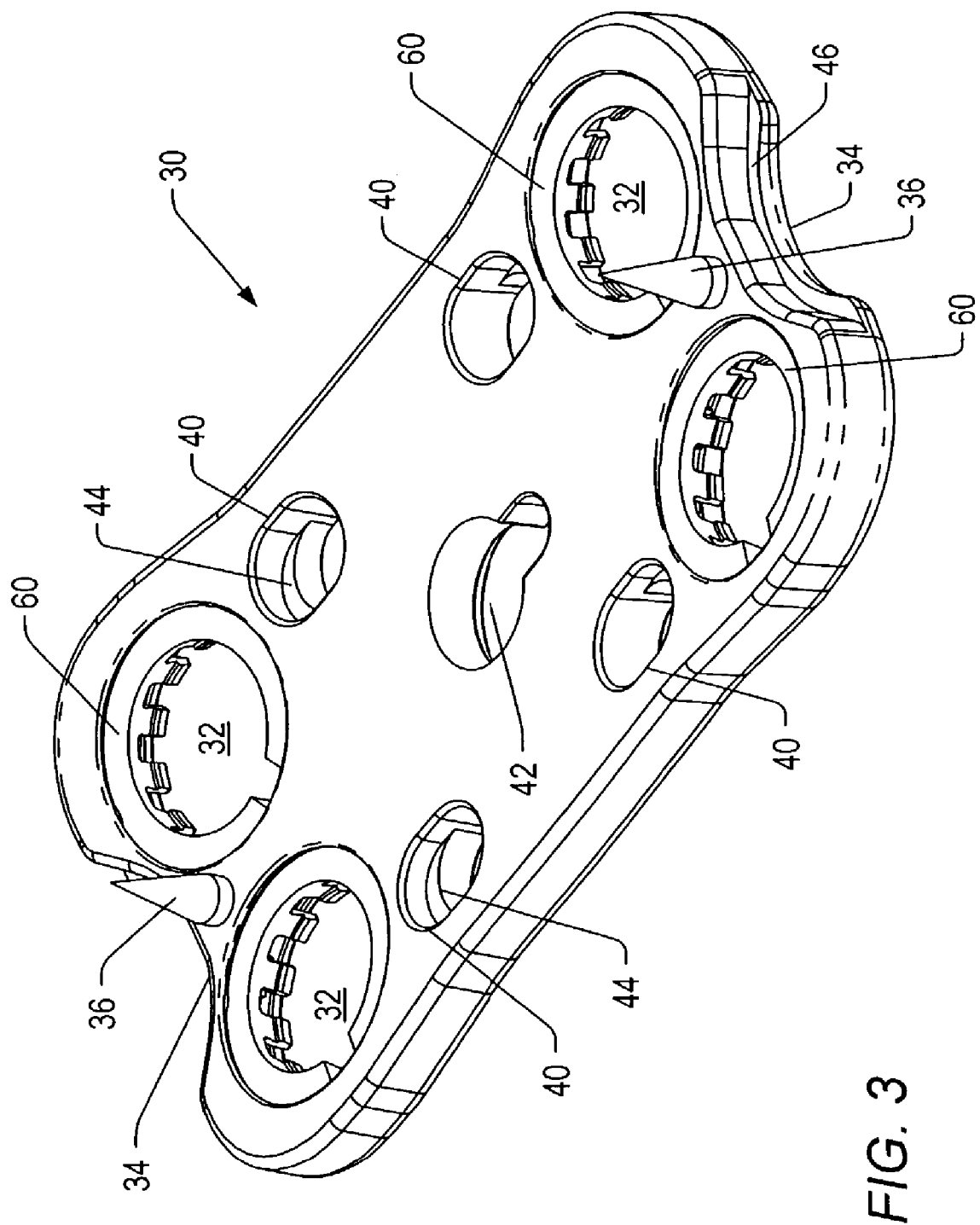
FIG. 3 depicts a perspective view that emphasizes a bottom of an embodiment of a base plate for a bone plate system with retainers positioned in openings of the base plate.

FIG. 2 and FIG. 3 depict embodiments of base plate 30 with retainers positioned in openings 32. Base plate 30 may include extender plate mounts 40 and aperture 42. Extender plate mounts 40 may allow attachment of an extender plate to base plate 30 that is coupled to vertebrae. Extender plate mounts 40 may include ledges 44, as shown in FIG. 2 and FIG. 3. Portions of an extender plate may engage ledges 44 to inhibit undesired separation or movement of an extender plate relative to base plate 30.

In some embodiments, extender plate mount 40 may be located a set distance away from an adjacent opening 32 in base plate 30. A portion of a tool guide may be positioned in extender plate mounts 40 to stabilize the tool guide and position tool bores of the tool guide over openings 32 in an end of base plate 30. Drills and/or taps may be positioned through the tool bores to form openings in vertebrae during the installation procedure. After holes are formed and/or tapped in a vertebra below a first end of base plate 30, the tool guide may be removed. The same tool guide, or a different tool guide, may be positioned in extender plate mounts 40 adjacent a second end of base plate 30. A different tool guide may be used if fasteners to be inserted into openings formed in a vertebra are to be positioned at different angles relative to the base plate than the fasteners positioned in openings in the first end of the base plate.

Base plate 30 may include one or more apertures 42. Aperture 42 may allow for proper positioning of instrumentation (e.g., insertion instruments, drill and/or tap guides) during an installation procedure. Aperture 42 may be used as a viewport to allow viewing of an implant positioned between adjacent vertebrae. The presence of aperture 42 or apertures may help to reduce the overall weight of base plate 30. In some embodiments, a fastener may be positioned through aperture 42 to couple base plate 30 to a spinal implant, vertebra replacement construct, or other device positioned between vertebrae.

In some base plate embodiments, ledge 46 may be formed in indention 34 of base plate 30. Ledge 46 may engage a portion of an extender plate. Contact of ledge 46 with a portion of an extender plate may inhibit undesired separation of the extender plate from base plate 30 when the extender plate is coupled to the base plate.

Dimensions of base plates used in a bone plate system may depend on patient characteristics as well as the number of vertebrae to be stabilized. Reducing the profile of a base plate positioned on a spine may decrease the risk of damage to surrounding tissue. A base plate may be relatively thin, but the base plate may be thick enough to allow an extender plate to be coupled to the base plate.

Base plates may be curved to conform to lordotic curvature of a spine and/or to medio-lateral curvature of vertebrae. Several different base plates may be provided to a surgeon who will perform an installation procedure for a bone plate system. The base plates may have various widths, lengths, and/or curvatures. In some embodiments, a plate bender may be provided in an instrumentation set to allow a base plate to be bent to accommodate a patient's lordotic curvature. In some embodiments, plates may be provided with pre-established lordotic curvatures. For example, plates may be provided with lordotic angles from about 0° to about 18° in about 3° increments. For example, a base plate for stabilizing vertebrae may have a length of about 28 mm, a maximum width of about 15 mm, and a 12° curvature preformed in the base plate. Base plates may include indicia showing the amount of curvature included in the plate. Having a preformed curvature in a base plate may eliminate some plate stress that would be present in a base plate that is contoured in an operating arena.

Figure 4:
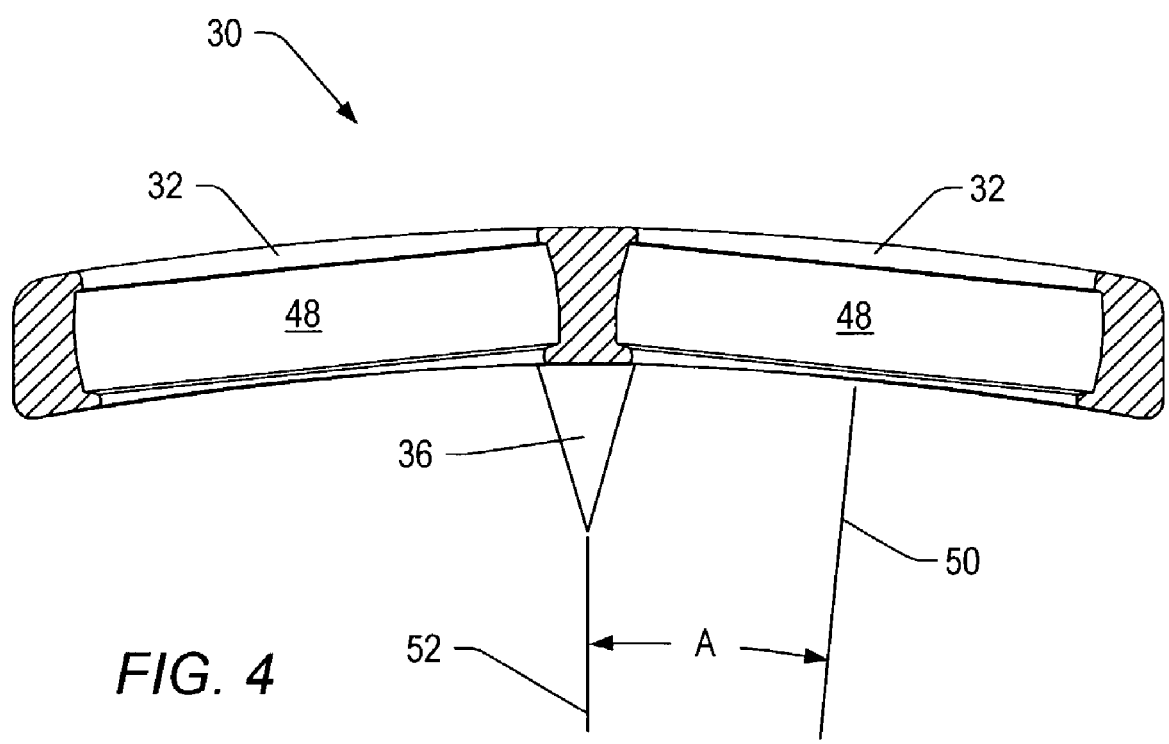
FIG. 4 depicts a cross-sectional end view of an embodiment of a base plate taken substantially along plane 4-4 shown in FIG. 2, without retainers positioned in openings of the base plate.

FIG. 4 depicts a cross-sectional view of an embodiment of base plate 30. Opening 32 in base plate 30 may include recessed portion 48. A portion of a retainer may fit in recessed portion 48 of opening 32. Recessed portion 48 may inhibit removal of a retainer from opening 32. A wall of opening 32 defining recessed portion 48 may have a spherical contour that corresponds to a spherical contour of a portion of a retainer. The spherical portion of the retainer may have a height that is less than a height of the recessed portion to allow for some polyaxial motion of the retainer when the retainer is positioned in recessed portion 48. In some embodiments, the polyaxial motion allowed by recessed portion 48 and a retainer may allow a fastener positioned in the retainer to be angled in a conic range of motion. In some embodiments, the range of motion of the fastener may be up to about 15° relative to a central axis normal to the center of the opening. In some embodiments, the range of motion of the fastener may be up to about 6° relative to a central axis normal to the center of the opening. In some embodiments, the range of motion of the fastener may be up to about 3° relative to a central axis normal to the center of the opening. Larger or smaller ranges of motion may be accommodated by controlling the difference between the height of the recess and the height of the portion of the retainer that resides in recessed portion 48.

Base plate 30 may include medio-lateral curvature. The medio-lateral curvature of base plate 30 may allow the base plate to substantially conform to the shape of vertebrae to which the base plate is to be coupled. In addition to or in lieu of a curvature formed in the base plate, an instrumentation set provided for an installation procedure may include a plate bender that allows for adjustment of medio-lateral curvature of a base plate.

Openings 32 in base plate 30 may be formed at a bias in the base plate. The bias may allow fasteners positioned through openings 32 to be oriented at desired angles relative to base plate 30. As depicted in FIG. 4, central axis 50 of opening 32 may form angle A relative to central axis 52 of base plate 30. Angle A may vary from about 0° (i.e., opening 32 is substantially parallel to central axis 52 of base plate 30) to about 15°. In some embodiments, the bias of openings 32 may be towards a center of base plate 30. For example, base plate 30 may be formed with openings that are biased at about 6° towards central axis 52. In some embodiments, the bias of the openings may be away from the center of the base plate towards sides of the base plate. In some embodiments, one opening may be biased towards the center of the base plate while a second opening may be biased away from the center towards a side of the base plate.

In addition to openings having no bias, or some bias towards or away from sides of a base plate, openings may also be biased towards or away from ends of the base plate. In an embodiment, openings in a caudal end of a base plate have substantially no bias (i.e., a neutral bias) while openings in a cephalic end of the base plate have a bias towards the cephalic end of the plate. The bias of an opening towards an end of a base plate may be less than about 15°, less than about 10°, less than about 6°, less than about 3°, or substantially 0° (i.e., neutral bias) relative to a central axis of the opening. Having a base plate with desired bias in caudal and cephalic openings, as well as having retainers that allow for angulation of fasteners positioned through the retainers, may help to inhibit pullout of an installed plate system from vertebrae during ordinary and/or unusual motion of a patient.

A base plate that includes different bias in openings in a cephalic end and a caudal end may include indicia to indicate which end of the base plate is the cephalic end and which end is the caudal end. For example, a base plate that includes different bias in openings in the cephalic end and in the caudal end may include an arrow etched, printed, or otherwise formed in a top surface of the base plate that points towards the cephalic end of the base plate.

Figure 5:
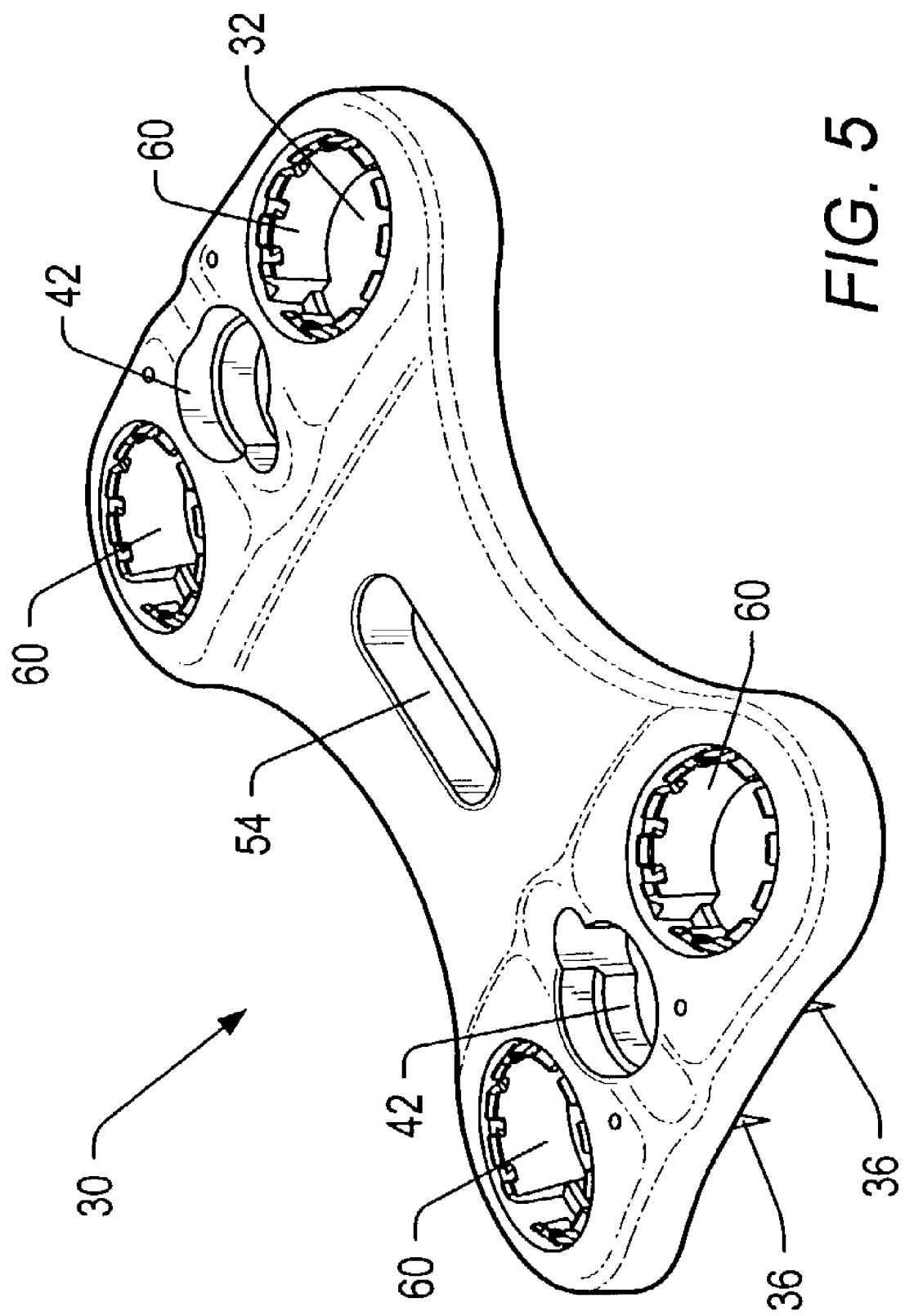
FIG. 5 depicts a perspective view of an embodiment of a base plate for a bone plate system.

Base plate 30 may have a large enough width to secure and stabilize vertebrae, but the width should be relatively small to minimize interference with surrounding tissue when the base plate is installed in a patient. The width should be small enough to avoid overhang of vertebrae to which the base plate is attached. Base plate 30 may have a variable width. A variable width base plate may provide a large viewing area and have less weight than a substantially constant width base plate. FIG. 5 depicts an embodiment of a base plate having a variable width. A maximum width of a base plate for cervical vertebrae may be less that about 40 mm. In some embodiments, a maximum width of a base plate for cervical vertebrae may be less than or equal to about 30 mm. The width of a base plate may depend on various patient characteristics and the region of the spinal column being stabilized.

A base plate may have a small thickness (i.e., height) to minimize interference of the base plate with adjacent tissue after insertion. The thickness of the base plate should also be small to allow for attachment of an extender plate without the combination of the extender plate and the base plate being too thick. A thickness of a base plate may be variable. A maximum thickness of base plate 30 may be adjacent to openings 32 through the base plate. A minimum thickness of a base plate may be present in a middle portion of the base plate. In some embodiments, base plate 30 may have a maximum thickness of less than or equal to about 3.5 mm. In some embodiments, the maximum thickness of base plate 30 may be less than or equal to about 2.4 mm. In some embodiments, the maximum thickness may be less than or equal to about 1.7 mm.

Some base plate embodiments may include central opening 54. Central opening 54 may provide visual and/or physical access to a spinal implant or bone graft material positioned between two vertebrae. In some embodiments, a surface of the base plate adjacent to central opening 54 may be recessed to accommodate a fastener head. A fastener may couple a spinal implant to a base plate. The recessed portion may minimize or eliminate a height of the fastener that extends above the base plate. Central opening 54 may have a circular, rectilinear, triangular, oblong, or irregular shape. In some embodiments, a retainer may be positioned in a central opening.

Figure 6:
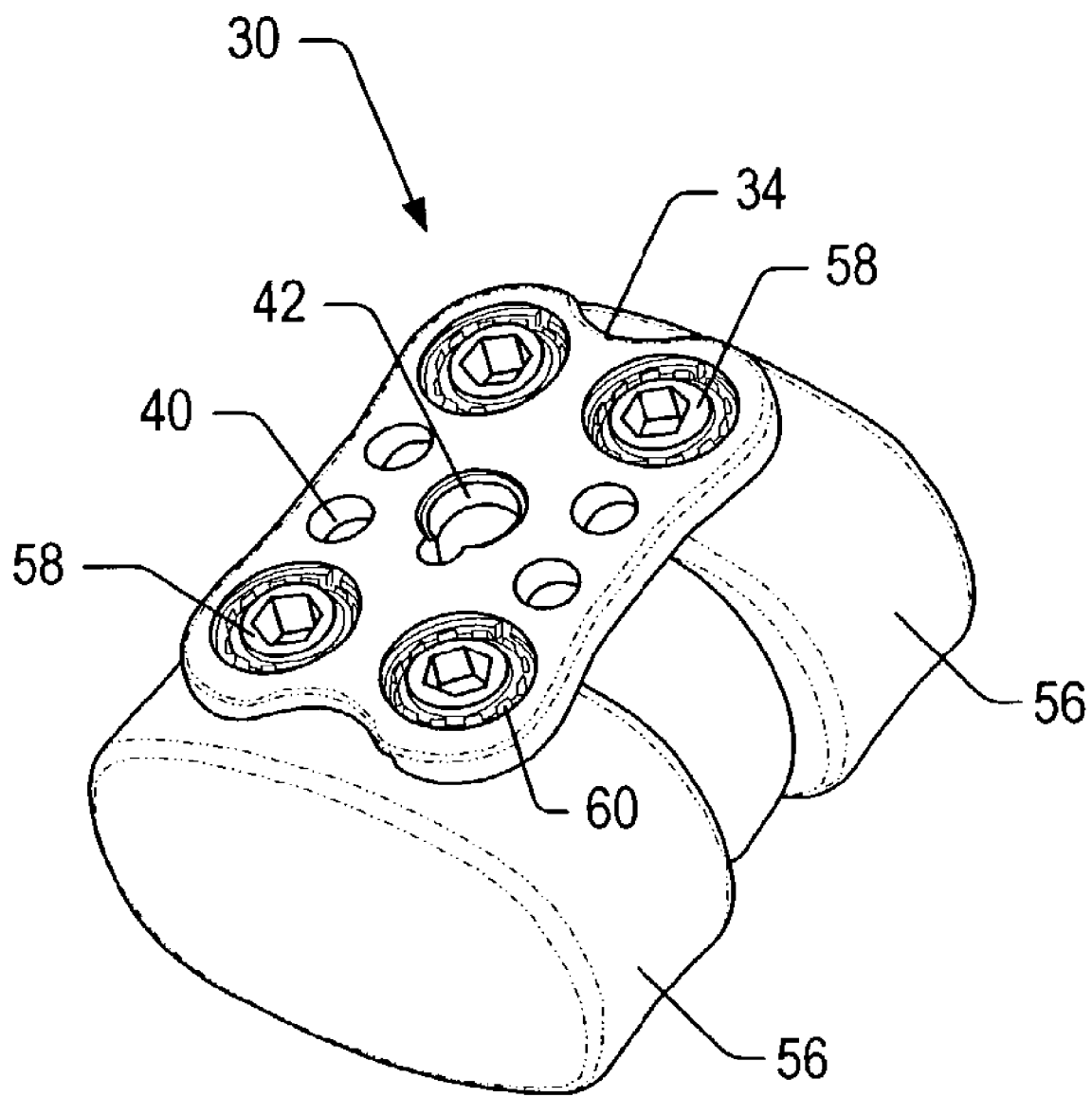
FIG. 6 depicts a perspective view of an embodiment of a base plate for a bone plate system.

FIG. 6 depicts an embodiment of base plate 30 coupled to vertebrae 56. Curvatures of base plate 30 may conform to the surfaces of vertebrae 56. Fasteners 58 may be used to couple base plate 30 to vertebrae 56. In some embodiments, heads of fasteners 58 may reside below a top surface of base plate 30 when fasteners 58 couple the base plate to vertebrae 56.

A fastening system may be used to couple base plate 30 to vertebrae 56. A fastening system may include fastener 58 and retainer 60. Fasteners may couple base plate 30 to vertebrae 56. Retainer 60 may couple a fastener to a base plate (or extender plate) without the fastening system becoming fixedly attached to the plate. In an embodiment, the fastener is a bone screw and the retainer is a ring. When the bone screw is inserted into a vertebra, the bone screw and ring are able to rotate in the plate until the bone screw is fully inserted into the vertebra. The ring inhibits backout of the fastener from the plate should the bone screw connection be stripped, loosened, or rotated in a direction that would remove the bone screw from the plate. A removal tool may be inserted between a ring and a head of a fastener to allow a fastener to be removed from a plate should the need arise.

Figure 7:
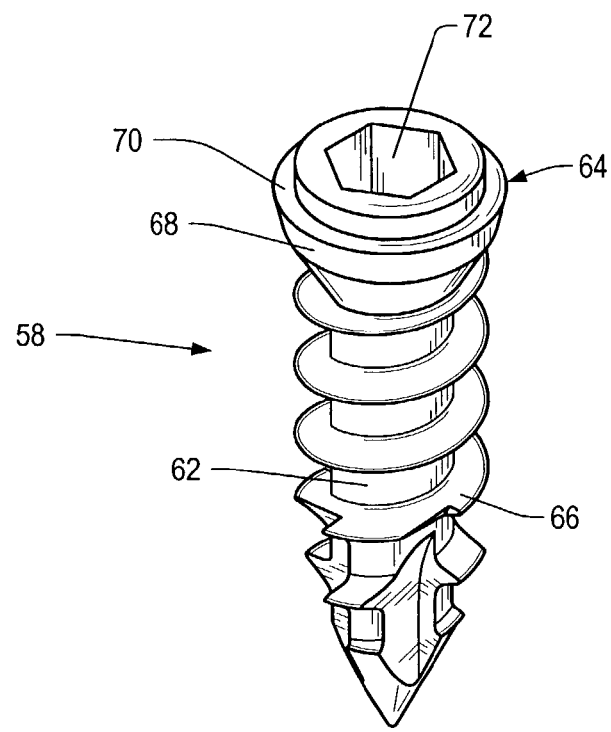
FIG. 7 depicts a perspective view of an embodiment of a fastener for a bone plate system.

FIG. 7 depicts a perspective view of an embodiment of fastener 58 that may be used to couple a base plate and/or an extender plate to a vertebra. Fasteners 58 may be provided in various lengths in an instrumentation set to accommodate variability in vertebral bodies. The fasteners may be color coded and/or stamped with indicia indicating lengths of the fasteners. For example, fasteners may be provided in 12 mm, 13 mm, and 14 mm lengths in some embodiments. The length of a fastener may be stamped and/or printed on a side of the fastener head. The 12 mm fasteners may have a gold color, the 13 mm fasteners may have a green color, and the 14 mm fasteners may have a magenta color. If desired, other colors may be used.

Fastener 58 may include shank 62 and head 64. In some embodiments, shank 62 may include threading 66 to engage vertebral bone. In some embodiments, shank 62 includes self-tapping starts to facilitate insertion into a vertebra. In other embodiments, shank 62 does not include self-tapping starts. In some embodiments, fasteners provided in an instrumentation set may have substantially the same thread profile. In some embodiments, various fasteners provided in an instrumentation set have different thread profiles. In an embodiment, a thread may have about a 4 mm major diameter and about a 2.5 mm minor diameter with a cancellous thread profile. Fasteners 58 with other thread dimensions and/or thread profiles may also be used. A thread profile of the fasteners may allow for maximizing bone purchase.

Rescue fasteners may be provided in an instrumentation set. A rescue fastener may be positioned in a deformed fastener opening in a vertebra. The rescue thread may have the same thread pitch as regular fasteners. The rescue fasteners may have a larger thread major diameter and the same thread minor diameter as threading of regular fasteners. For example, if a regular fastener has about a 4 mm major thread diameter and about a 2.5 mm minor thread diameter, a corresponding rescue fastener may have a 4.5 mm major thread diameter thread and about a 2.5 mm minor thread diameter. Rescue fasteners may be separated from regular fasteners in an instrumentation set. The rescue fasteners may be a distinctly different color than regular fasteners. For example, rescue fasteners may be blue. Different fastener lengths may be indicated by different shades of the color of the rescue fastener.

In some embodiments, fastener head 64 may include tapered section 68, engagement section 70, and head opening 72. In some embodiments, engagement section 70 is located at or near a top of tapered section 68. In some embodiments, engagement section 70 may be a recessed portion in head 64. Projections of a retainer may extend over engagement section 70 to inhibit backout of a fastener from a base plate.

Figure 8:
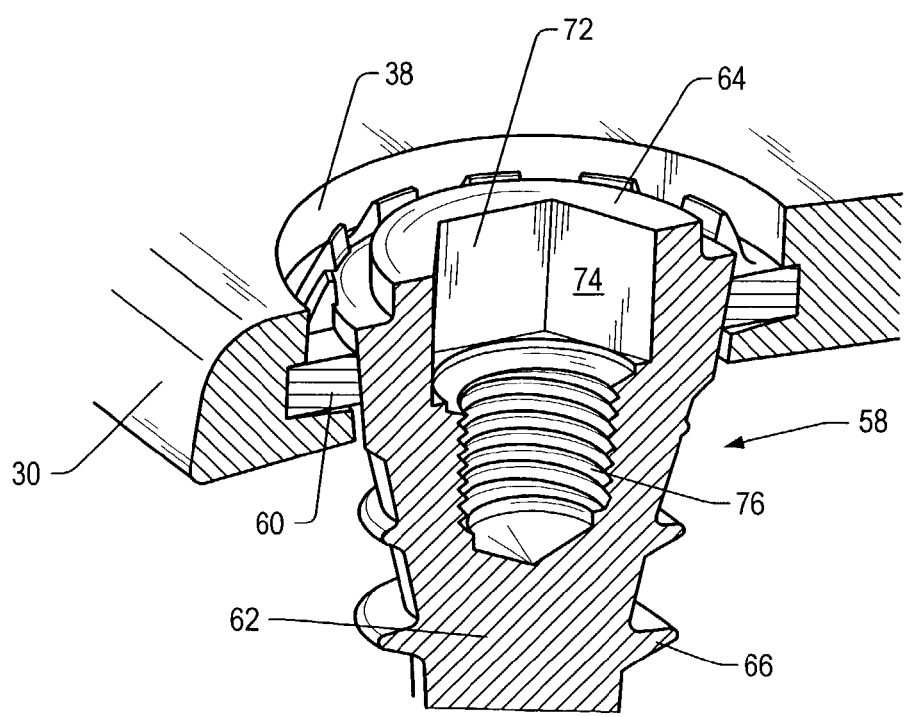
FIG. 8 depicts a cross-sectional representation of a portion of an embodiment of a fastener in a bone plate system.

As shown in FIG. 8, head opening 72 may include tool portion 74 and recessed portion 76. An insertion tool (e.g., a hex wrench or other tool that mates with the opening) may be inserted into tool portion 74 to allow fastener 58 to be driven into a vertebra. In an embodiment, recessed portion 76 may include threading. In some embodiments, threading in recessed portion 76 may have an orientation that is the same as the orientation of fastener threading 66. In other embodiments, threading in recessed portion 76 may have an orientation opposite to the orientation of fastener threading 66.

Retainer 60 may be positioned in opening 32 of base plate 30. A retainer may be any member capable of fitting between an inner surface of an opening in a plate and a fastener. Retainers may be made of biocompatible materials including metals (e.g., titanium and titanium alloys), plastics, and/or composites. Using retainers to couple fasteners to a bone plate system may inhibit backout of fasteners from a plate. Retainers may allow fasteners positioned in the retainers to be angulated relative to the plate.

In some embodiments, retainers may be placed in openings of a plate before a surgical procedure is begun. The size of the retainers and the size of the openings may inhibit removal of the retainers from the plate. In other embodiments, retainers may be coupled to fasteners before a surgical procedure is begun. Positioning retainers in openings, or coupling retainers to fasteners, prior to a surgical procedure may facilitate overall efficiency of an insertion procedure by eliminating the need to position the retainers during the procedure. Using pre-positioned retainers may minimize the possibility of dropping a retainer during an installation procedure.

Figure 9:
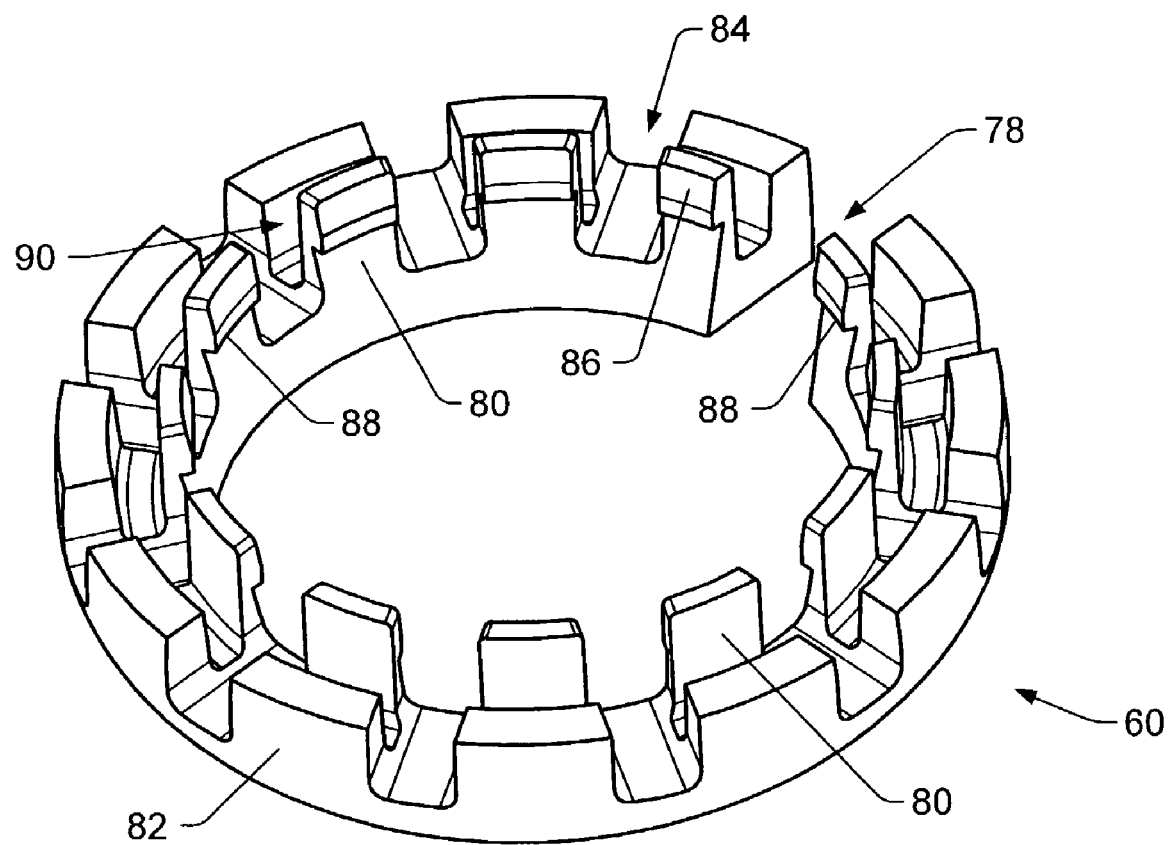
FIG. 9 depicts a perspective view of an embodiment of a retainer for a bone plate system.

FIG. 9 depicts an embodiment of retainer 60. Retainer 60 may include gap 78, fingers 80, and back portion 82. Gap 78 may allow for compression and expansion of retainer 60. In an embodiment, retainer 60 may be compressed to reduce a diameter of the retainer. In some embodiments, a compression tool may facilitate compression of a retainer so that the retainer may be inserted into a plate. The compression tool may also be used to remove a retainer from a plate. The compression tool may include arms with portions that fit in slots 84 of retainer 60 that are near gap 78. Ends of the arms may engage inner surfaces of retainer 60 to inhibit the arms of the compression tool from extending beyond an outer surface of the retainer. A handle of the compression tool may be squeezed to reduce gap 78 and compress the retainer.

When compressed, retainer 60 may be positioned in an opening of a plate. Retainer 60 may be released to allow the diameter of the retainer to expand. When expanded in the opening, the size of retainer 60 may inhibit removal of the retainer from the opening. Retainers may be pre-positioned in openings of plates to avoid the need to place retainers in plates during a plate installation procedure.

Figure 10:
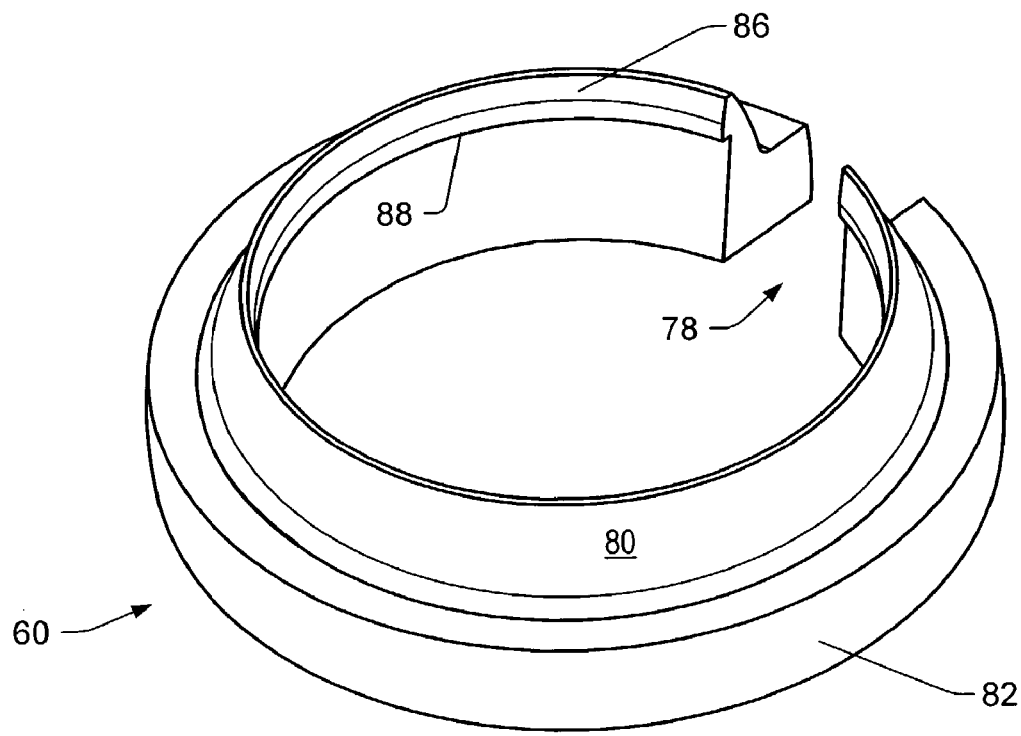
FIG. 10 depicts a perspective view of an embodiment of a retainer for a bone plate system.

Fingers 80 of retainer 60 may couple the retainer to a fastener positioned through the retainer. When the fastener is initially inserted into retainer 60, a head of the fastener may deflect fingers 80 outwards towards back portion 82 of the retainer. Tapered portion 86 of fingers 80 may facilitate insertion of a fastener in retainer 60. After engagement section 70 (shown in FIG. 7) passes shoulder 88 of fingers 80, the fingers may deflect inwards. Shoulders 88 of the fingers may contact an engagement section of the fastener if the fastener moves in a direction out of the opening to inhibit backout of the fastener from a base plate. In some retainer embodiments, such as the embodiment depicted in FIG. 10, retainer 60 may include single finger 80 instead of a plurality of fingers.

Figure 11:
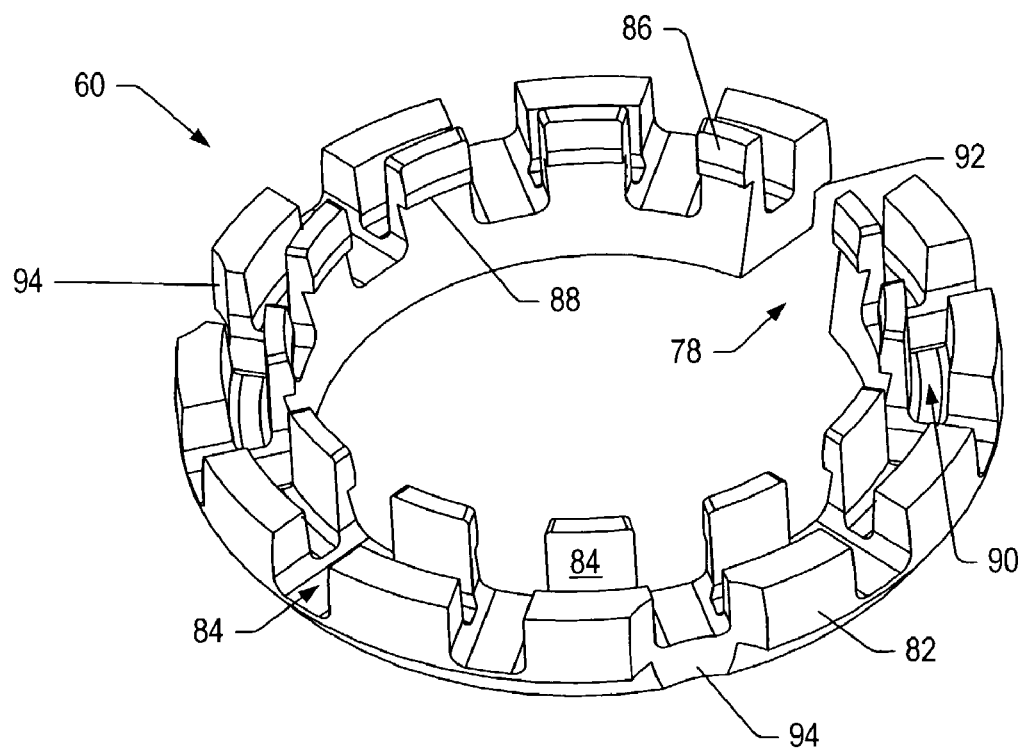
FIG. 11 depicts a perspective view of an embodiment of a retainer for a bone plate system.

In some retainer embodiments, such as the embodiments depicted in FIG. 9 and FIG. 11, fingers 80 of retainer 60 may be separated from back portion 82 by gap 90. Separating back portion 82 from fingers 80 may allow retainer 60 to have a minimal height. In some retainer embodiments, such as the embodiment depicted in FIG. 11, back portion 82 of retainer 60 may include undercut portion 92. Undercut portion 92 may allow a recess in a base plate to have a small height.

Figure 12:
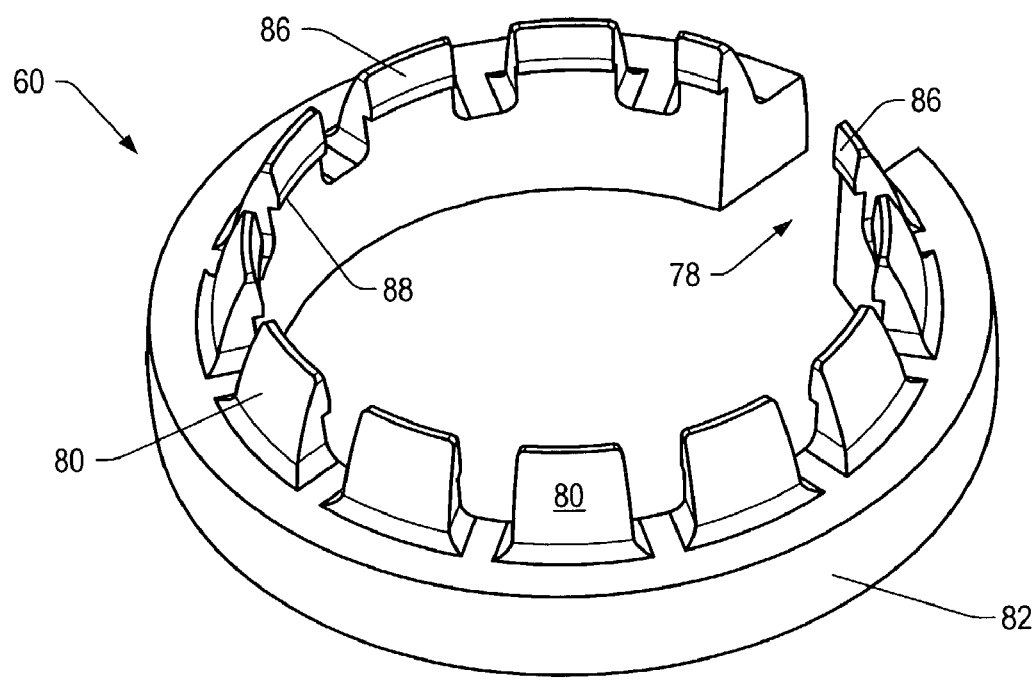
FIG. 12 depicts a perspective view of an embodiment of a retainer for a bone plate system.

Some retainer embodiments may not include a gap between a finger or fingers and a back portion of a retainer. For example, in the retainer embodiments depicted in FIG. 10, FIG. 12, and FIG. 13, fingers 80 are located adjacent to back portion 82 of retainer 60.

In some embodiments, a fastener head coupled to a base plate by retainer 60 may be inhibited from rising above the top surface of the base plate by interaction between back portion 82 and the recess of the base plate. Interaction between back portion 82 and the recess of the base plate may inhibit portions of retainer 60 from moving below a bottom surface of the base plate. In some embodiments, the outer surface of the back portion may be curved to substantially conform to the shape of the recess in the opening to allow a fastener positioned through the retainer to be set at a desired angle relative to a base plate.

Figure 13:
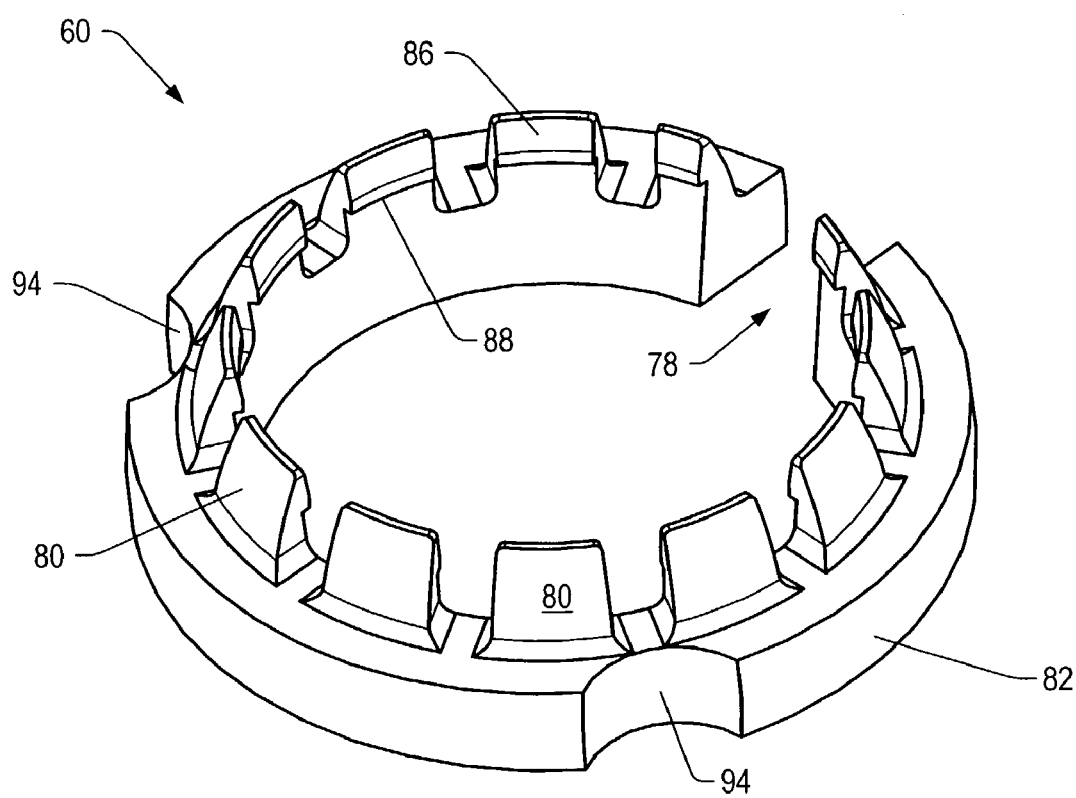
FIG. 13 depicts a perspective view of an embodiment of a retainer for a bone plate system.

As shown in FIG. 11 and FIG. 13, retainer 60 may include indentions 94. Indentions 94 may promote flexibility of retainer 60. Flexibility of the retainer may facilitate insertion of the retainer into an opening of a base plate.

As shown in the embodiment depicted in FIG. 8, head 64 of fastener 58 may contact retainer 60. Fingers 80 may extend over engagement section 70 of the fastener. Retainer 60 may contact base plate 30 so that the fastener and retainer combination holds the base plate against a vertebra. Fastener 58 is able to rotate relative to retainer 60, and/or the retainer is able to rotate relative to base plate 30, until the fastener is driven into a vertebrae to a sufficient depth to pull the plate securely against the vertebra. If fastener 58 loosens in the vertebra, fingers 80 of retainer 60 will contact engagement section 70 of the fastener to inhibit backout of the fastener from base plate 30.

In some embodiments, a portion of the fastener may contact a portion of a base plate to inhibit passage of the fastener through the base plate. Contact of the fastener against the base plate allows the fastener to draw the base plate against a vertebra as the fastener is rotated in the base plate.

Figures 14, 15:
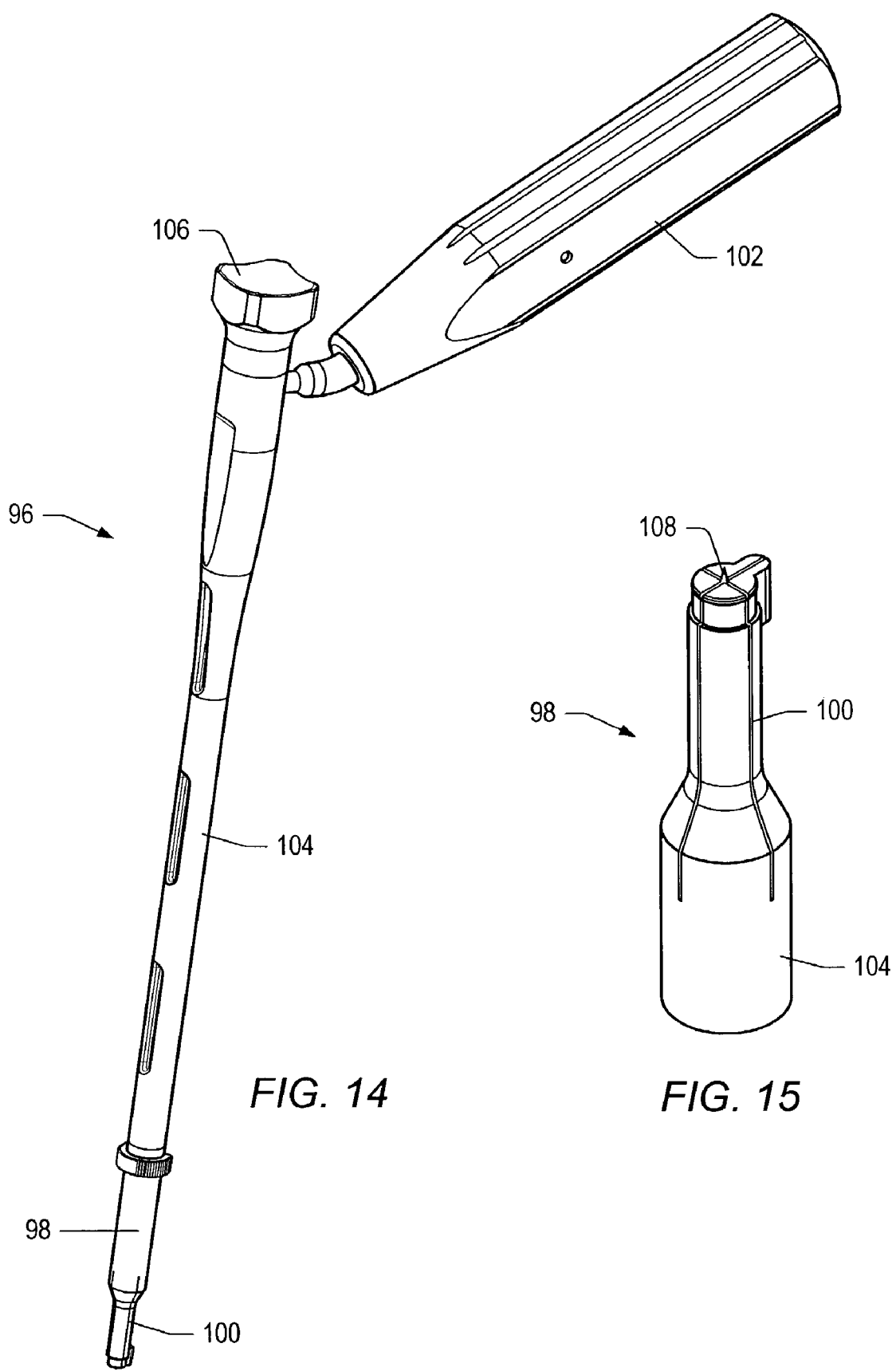
FIG. 14 depicts a perspective view of a plate insertion instrument.
FIG. 15 depicts an embodiment of a portion of a plate insertion instrument.

FIG. 14 depicts an embodiment of a plate insertion instrument. Plate insertion instrument 96 may include engagement end 98, slots 100, handle 102, shaft 104, and actuator surface 106. Engagement end 98 may fit in an aperture of a base plate (i.e., aperture 42 of base plate 30 as depicted in FIG. 2). Slots 100 may be compressed when engagement end 98 is placed in an aperture of a base plate to form a press-fit engagement between plate insertion instrument 96 and the base plate.

Handle 102 of plate insertion instrument 96 may extend away from shaft 104. Handle 102 may allow a base plate to be properly positioned on vertebrae in a surgical opening. When the base plate is positioned, a user may push or strike actuator surface 106 to drive at least one spike of the base plate into at least one vertebra. A press-fit connection between the base plate and plate insertion instrument 96 may be removed by moving the plate insertion instrument away from the base plate. In some procedures, a tamp or other instrument may be held against the base plate to make sure the press-fit connection is removed when plate insertion instrument 96 is lifted from the base plate.

FIG. 15 depicts a perspective view of an end portion of a plate insertion instrument. Engagement end 98 may include spike 108. In some embodiments, a plate insertion instrument may not include a spike.

Figure 16:
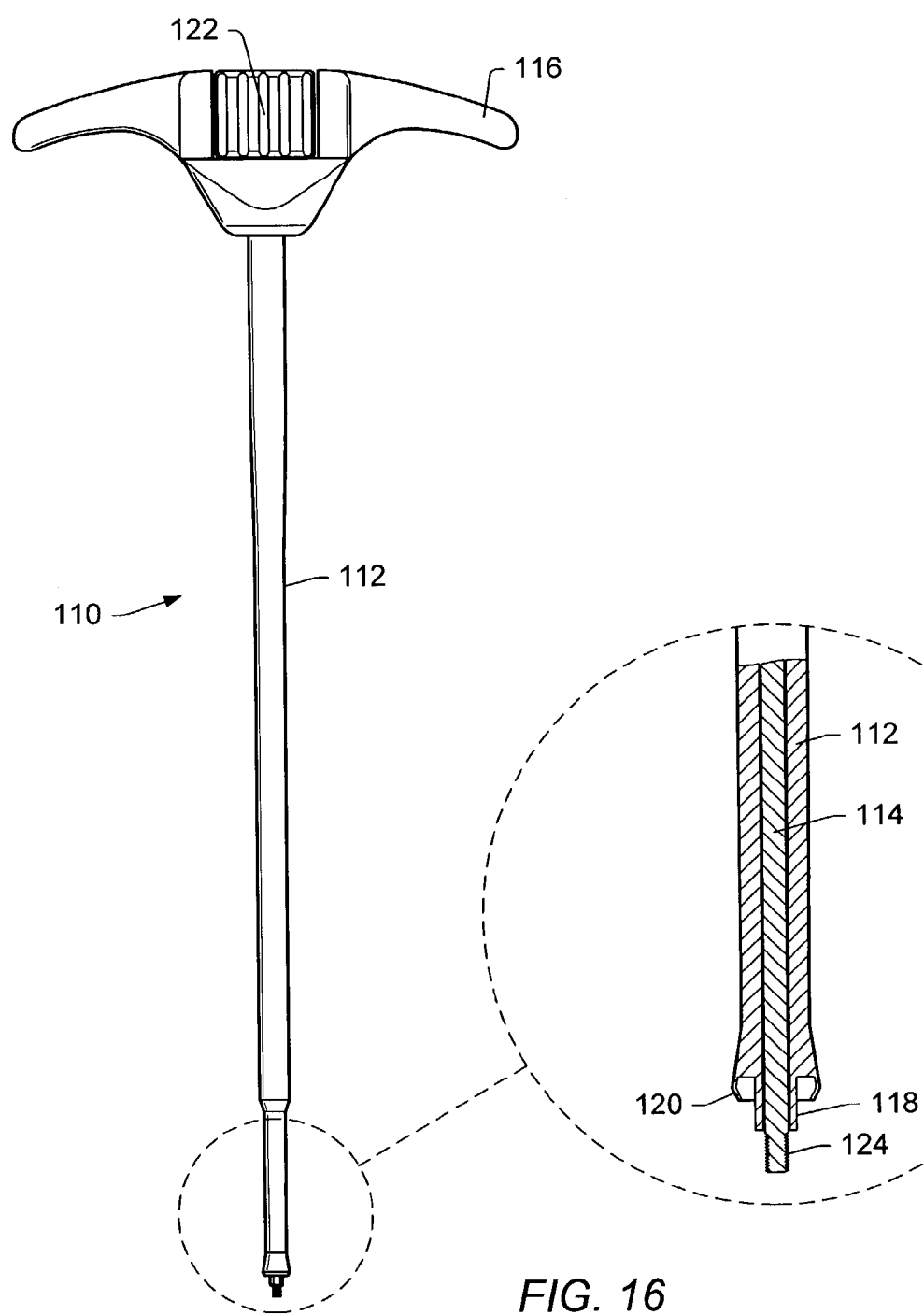
FIG. 16 depicts a front view of an embodiment of a fastener insertion tool, including an inset cross-sectional view of the tip of the insertion tool.

A fastener insertion tool may be used to insert a fastener through a retainer and into a vertebra. FIG. 16 depicts an embodiment of fastener insertion tool 110. Fastener insertion tool 110 may include outer shaft 112 and inner shaft 114. Outer shaft 112 may include handle 116. Handle 116 may be a grip that allows a user to securely hold insertion tool 110 and easily apply sufficient torque to a fastener to drive the fastener into a vertebra. Outer shaft 112 may have sufficient length to allow handle 116 to be operated above an incision in a patient while maintaining good visibility of the operating area.

An end of outer shaft 112 may include drive section 118 and tapered section 120. Drive section 118 may mate with a tool portion of a fastener. When drive section 118 is placed in a tool portion of a fastener, rotation of handle 116 will rotate the fastener. Tapered section 120 may contact portions of a retainer during insertion or removal of a fastener. Tapered section 120 may force fingers of a retainer outwards. Tapered section 120 may allow a fastener to be removed from the retainer.

A portion of inner shaft 114 may interact with a stop in handle 116 or another portion of outer shaft 112 to inhibit separation of the inner shaft from the outer shaft, while still allowing for some axial movement of the inner shaft relative to the outer shaft. Inner shaft 114 may have knob 122 at a first end and threaded section 124 at a second end. Threaded section 124 may mate with threading in a recessed portion of a fastener.

To use fastener insertion tool 110, knob 122 may be moved away from drive section 118 of outer shaft 112. Drive section 118 may be placed in a tool portion of a fastener. Knob 122 may be moved towards drive section 118 and rotated so that threaded section 124 of inner shaft 114 engages threading in a recessed portion of the fastener. Attaching threaded section 124 of inner shaft 114 to threading in recessed portion of the fastener couples the fastener to insertion tool 110 and inhibits unintentional separation of the fastener from the fastener insertion tool.

Fastener insertion tool 110 may be used to position the fastener through a retainer positioned in a base plate. Handle 116 of fastener insertion tool 110 may be rotated to drive the fastener into a vertebra. Handle 116 may be rotated until interaction of the fastener with the retainer and/or the base plate draws the base plate against the vertebra. Knob 122 may be rotated in a direction to separate threading of inner shaft 114 from threading in the recessed portion of the fastener. Fastener insertion tool 110 may then be removed from the fastener.

To remove a fastener from a vertebra and from a base plate, drive section 118 of fastener insertion tool 110 may be placed in the tool portion of the fastener to be removed. Knob 122 may be rotated to engage threading of inner shaft 114 with threading in a recessed portion of the fastener. Knob 122 may include indicia that indicate the proper rotational direction to turn the knob to couple inner shaft 114 to the fastener. As threading of inner shaft 114 engages threading in the fastener, tapered section 120 of outer shaft 112 may force fingers of the retainer outwards. When the inner shaft is secured to the fastener, handle 116 may be rotated to remove the fastener from the vertebra, base plate, and retainer.

Retainers may be positioned in openings of a base plate prior to insertion of the base plate into a patient. The base plate may be positioned on vertebrae. Spikes of the base plate may be driven into the vertebrae to temporarily fix the plate relative to the vertebrae. In some procedures, a drill may be used to form initial openings in the vertebrae at desired angles for fasteners. In some procedures, drill guides may be used to obtain desired angles. In some embodiments, openings may be formed without the use of drill guides. A fastener may be coupled to an insertion tool. A shank of the fastener may be positioned through a retainer in the base plate and into an opening formed in a vertebra. The insertion tool may be rotated to drive the fastener into the vertebra. A head of the fastener may expand the retainer. A tapered section of the head may facilitate expansion of the retainer. When the fastener is driven into the vertebra to a certain depth, an engagement section of the head will pass fingers of the retainer. The fastener may be driven further into the vertebra to draw and secure the base plate against the vertebra. The insertion tool may be removed from the fastener. The insertion tool may be used to insert other fasteners that secure the base plate to the vertebrae.

After insertion of a fastener to couple a base plate to a vertebra and after removal of the insertion tool, portions of fingers of a retainer may extend over an engagement section of the fastener. Should the fastener try to move out of the base plate, the engagement section will contact the portions of the fingers that extend over the engagement section to inhibit backout of the fastener from the base plate.

When a fastener is driven into a vertebra, a retainer contacted by the fastener may contact the base plate so that the fastener securely holds the base plate against the vertebrae. In some embodiments, a head of the fastener may expand the retainer so that a back portion of the retainer contacts a wall forming an opening in a base plate. In some embodiments, a portion of a fastener may contact a portion of a base plate to securely couple the base plate to vertebrae.

In some embodiments, there is enough friction between the retainer and the base plate so that only the fastener rotates when the fastener is driven into the vertebra. In some embodiments, the fastener may rotate along with the retainer when the fastener is driven into a vertebra.

Figure 17:
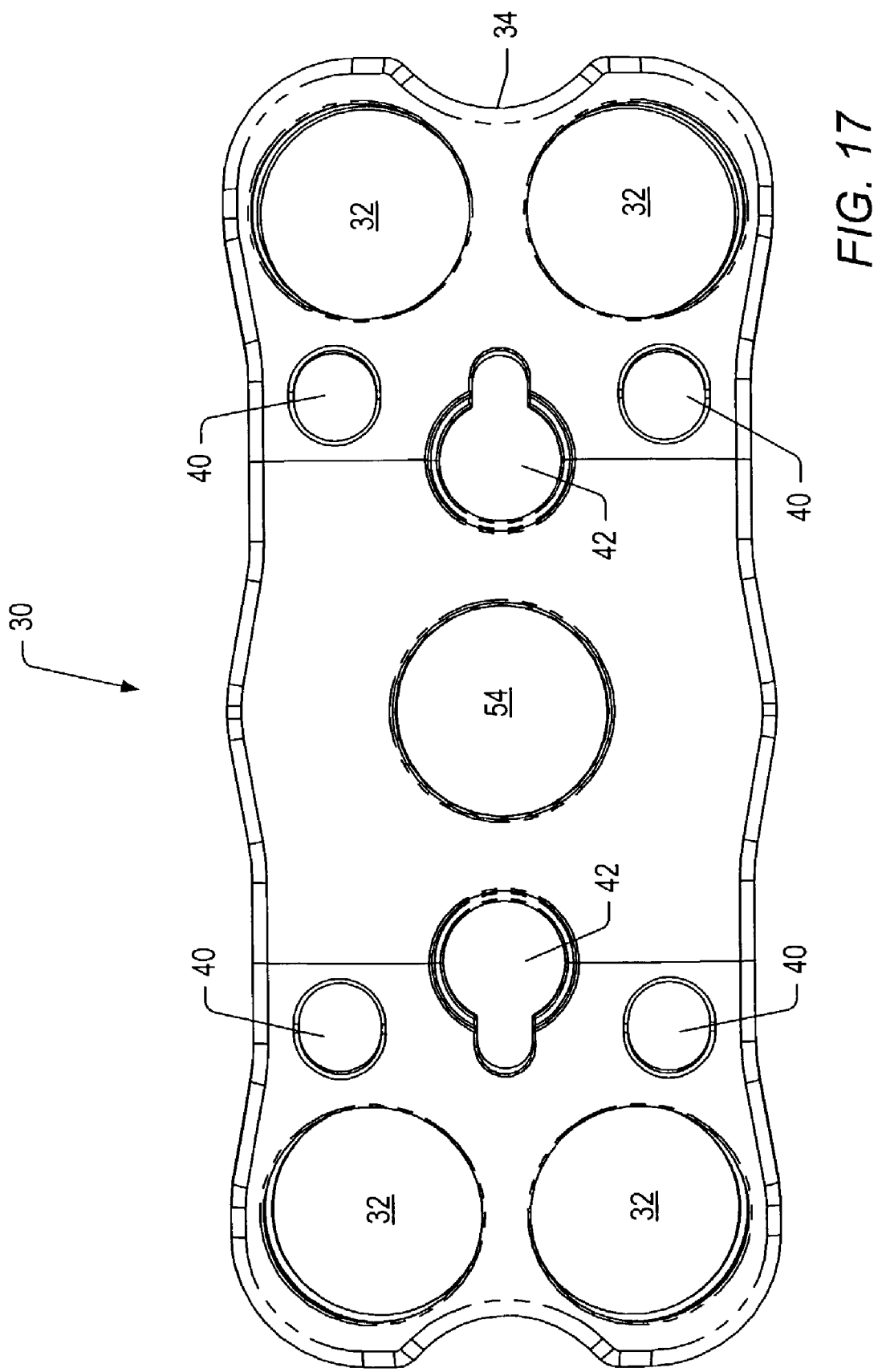
FIG. 17 depicts a top view of an embodiment of a base plate for a bone plate system.

FIG. 17 depicts an embodiment of base plate 30 that may be used to couple together two vertebral levels (i.e., three vertebrae). Openings 32 are positioned at both ends of plate 30. Base plate 30 may also include central opening 54 positioned proximate a midpoint of the base plate. A fastener may be positioned through central opening 54 to couple base plate 30 to a vertebra or a vertebra replacement construct.

Figure 18:
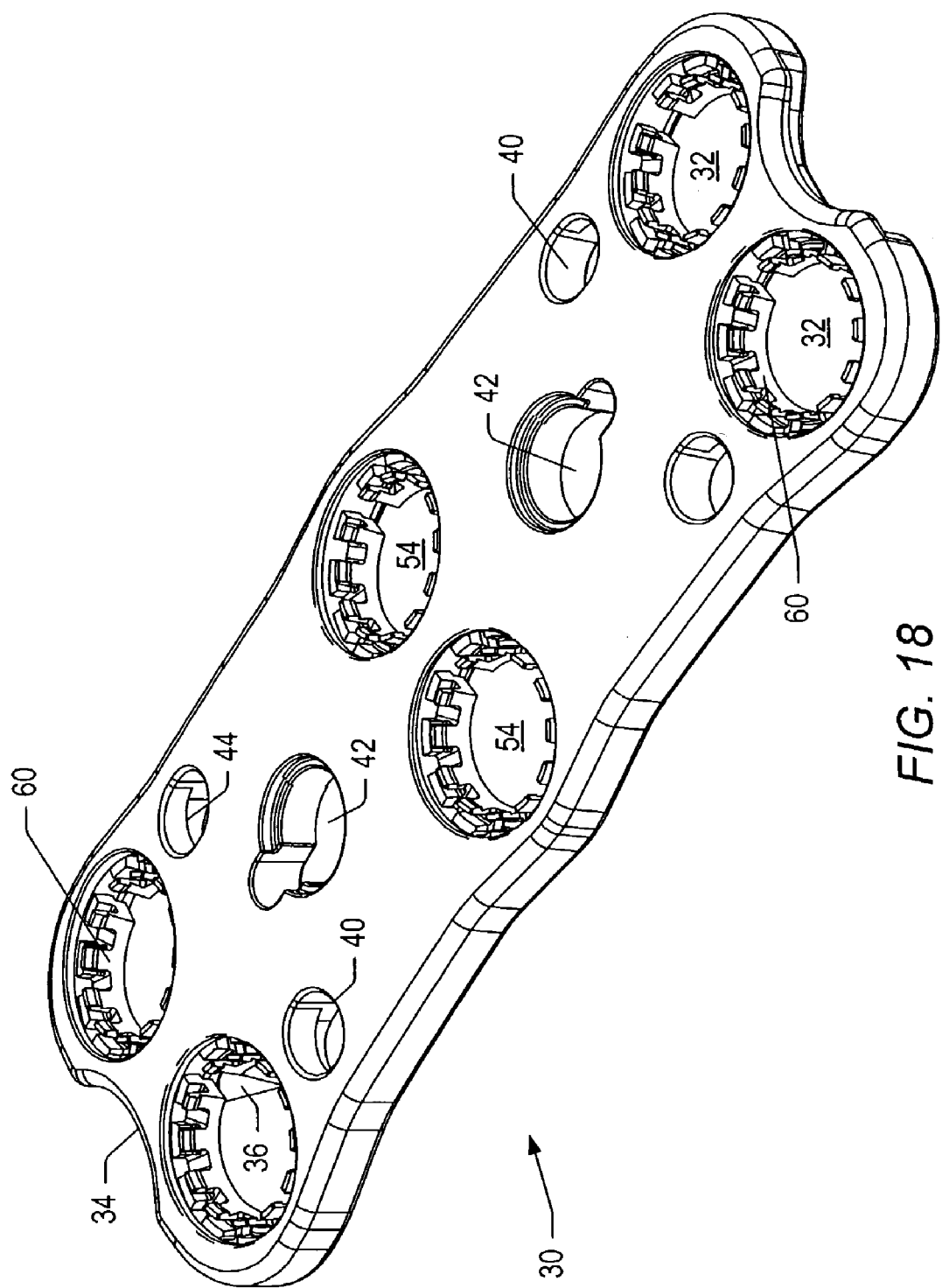
FIG. 18 depicts a perspective view of an embodiment of a base plate for a bone plate system.

FIG. 18 depicts an embodiment of a base plate with two central openings 54. Retainers 60 may be positioned in openings 32 and/or central openings 54. Extender plate mounts 40 may include ledges 44. Base plate 30 may include apertures 42 and/or indentions 34.

Figure 19:
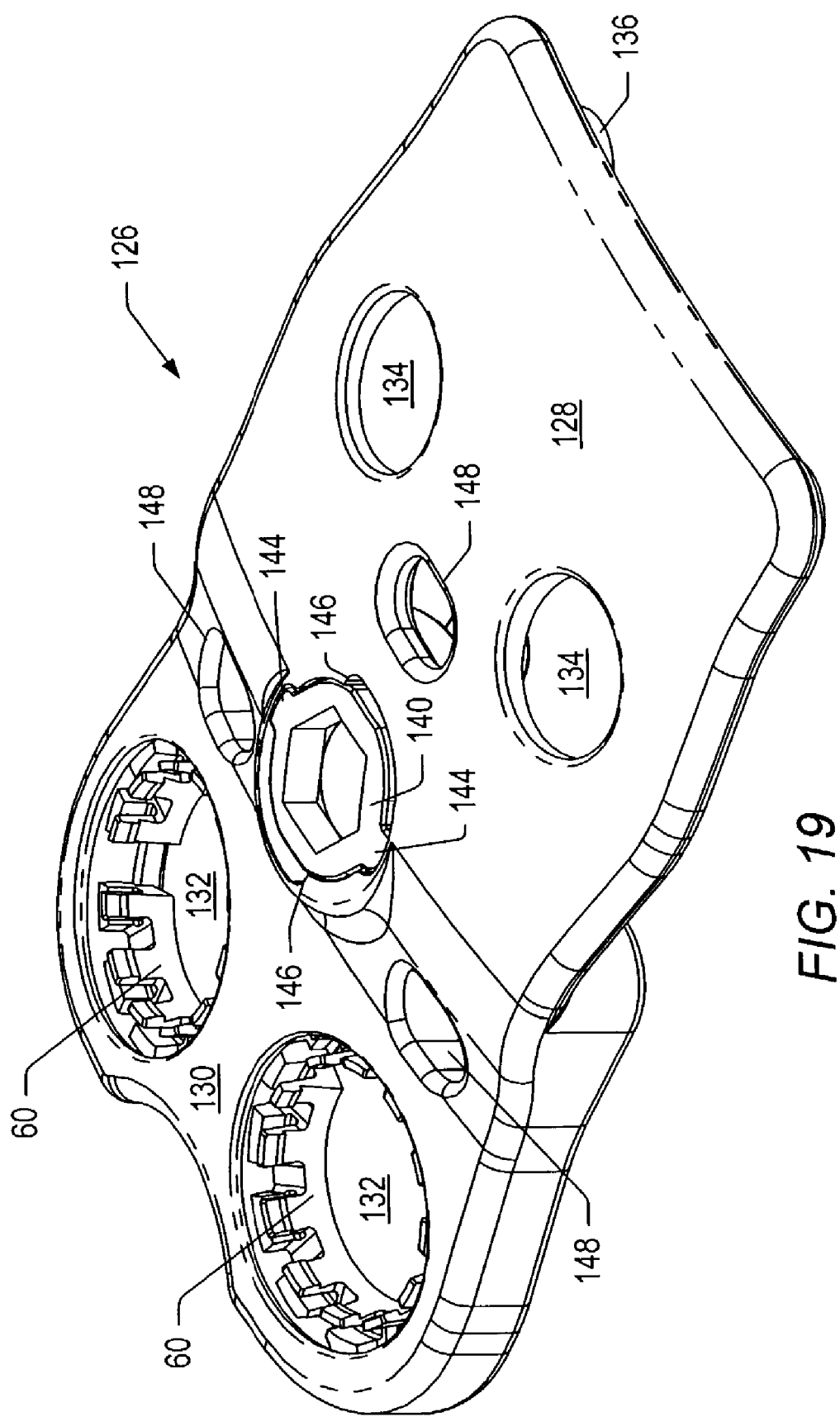
FIG. 19 depicts a perspective view of an embodiment of an extender plate for a bone plate system.
Figure 20:
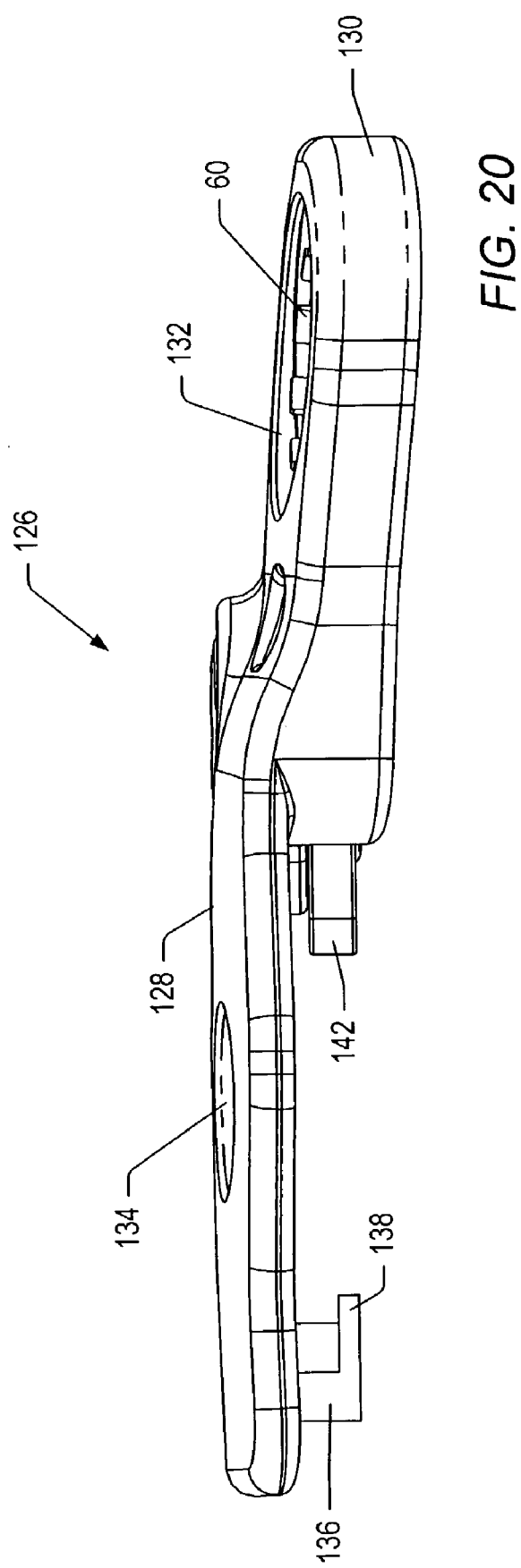
FIG. 20 depicts a side view of an embodiment of an extender plate for a bone plate system.

Some time after insertion of a base plate, further stabilization of the spine may become necessary. If changes occur that require further stabilization in close proximity to a previously inserted base plate, an extender plate may be added to an installed bone plate system to stabilize additional vertebral levels. FIG. 19 and FIG. 20 depict embodiments of extender plate 126. Extender plate 126 may include overlay section 128 and coupling section 130.

A thickness of extender plate 126 may vary across a length of the plate. In some embodiments, coupling section 130 may have an average thickness of less than about 5.0 mm. In some embodiments, an average thickness of coupling section 130 may be less than about 2.5 mm. For example, coupling section 130 may have an average thickness of about 1.7 mm. Overlay section 128 may be positioned over a portion of a base plate. Overlay section 128 may have a reduced thickness to minimize the profile of the bone plate system formed by the combination of the base plate with extender plate 126. Overlay section 128 may have an average thickness substantially less than an average thickness of coupling section 130.

Coupling section 130 may be used to attach extender plate 126 to a vertebra. Fasteners may be positioned through fastener openings 132 in coupling section 130 to fix extender plate 126 to a vertebra. In some embodiments, openings 132 include recesses that accept back portions of retainers 60 positioned in the openings. In some embodiments, openings 132 allow for fasteners to be set relative to extender plate 126 at a substantially fixed angle. In some embodiments, openings 132 may allow for angulation of retainers 60 and fasteners positioned in the openings. In some embodiments, the range of angulation may allow a fastener to be set into a bone at a desired angle in a conic range allowed by angulation of the retainer in the opening. For example, an opening in an extender plate for attachment to a caudal end of a base plate may allow for about 6° of angulation of a fastener positioned in the opening relative to a central axis through the opening. The fastener may be positioned in the vertebra at an angle of about 4° relative to the central axis of the opening and away from the caudal end of the base plate and about 3° towards a nearest side of the extender plate. Openings that allow for other angulation values may be formed in an extender plate.

In some embodiments, a recess may be formed in a fastener opening. A portion of a retainer may reside in the recess. The recess may be biased relative to an end and/or a side of the extender plate. The bias may be from about 1° to about 10°. In an embodiment, a bias of a recess in an opening of an extender plate may allow a retainer and a fastener to have an initial angle in a cephalic direction of about 6° relative to a central axis of the opening. If the fastener openings also allow for about 6° of angulation, a fastener positioned through a retainer in the opening may be angled from about 0° to about 12° in a cephalic direction. The recesses may also allow for angulation of about 6° towards sides of the plate.

Overlay section 128 may extend over at least a portion of a base plate. In some embodiments, a lower surface of overlay section 128 may include depressions that correspond to locations of openings in a base plate to which extender plate 126 attaches. In other embodiments, such as the embodiments depicted in FIG. 19 and FIG. 20, overlay section 128 may include openings 134 that align with openings in a base plate to which extender plate 126 attaches. The depressions or openings 134 may provide room for portions of fasteners and/or retainers that extend above the base plate that the extender plate is to be attached to. In some embodiments, fasteners below depressions or openings 134 may be loosened during an extender plate insertion procedure to facilitate connecting the extender plate to the base plate.

Extender plate 126 may be coupled to a base plate by various coupling devices. The coupling devices may be positioned at various locations on the base plate and extender plate 126. Coupling devices may include, but are not limited to, protruding members (e.g., spikes, tabs, and/or shafts), recesses or openings that receive tabs or protruding members, and/or an engager or engagers (e.g., an engagement mechanism).

In the extender plate embodiments depicted in FIG. 19 and FIG. 20, extender plate 126 includes tabs 136 and an engagement mechanism. Tabs 136 fit in extender plate mounts 40 of base plate 30 (depicted in FIG. 2). Tabs 136 may include extended portion 138 as shown in FIG. 20.

When extender plate 126 is coupled to a base plate, tab 136 may slide in an extender plate mount so that ledge 44 (shown in FIG. 2) of base plate 30 is positioned between extended portion 138 and a bottom of the extender plate. Positioning ledge 44 between the bottom of extender plate 126 and extended portion 138 may inhibit undesired separation of the extender plate from the base plate.

Figure 21:
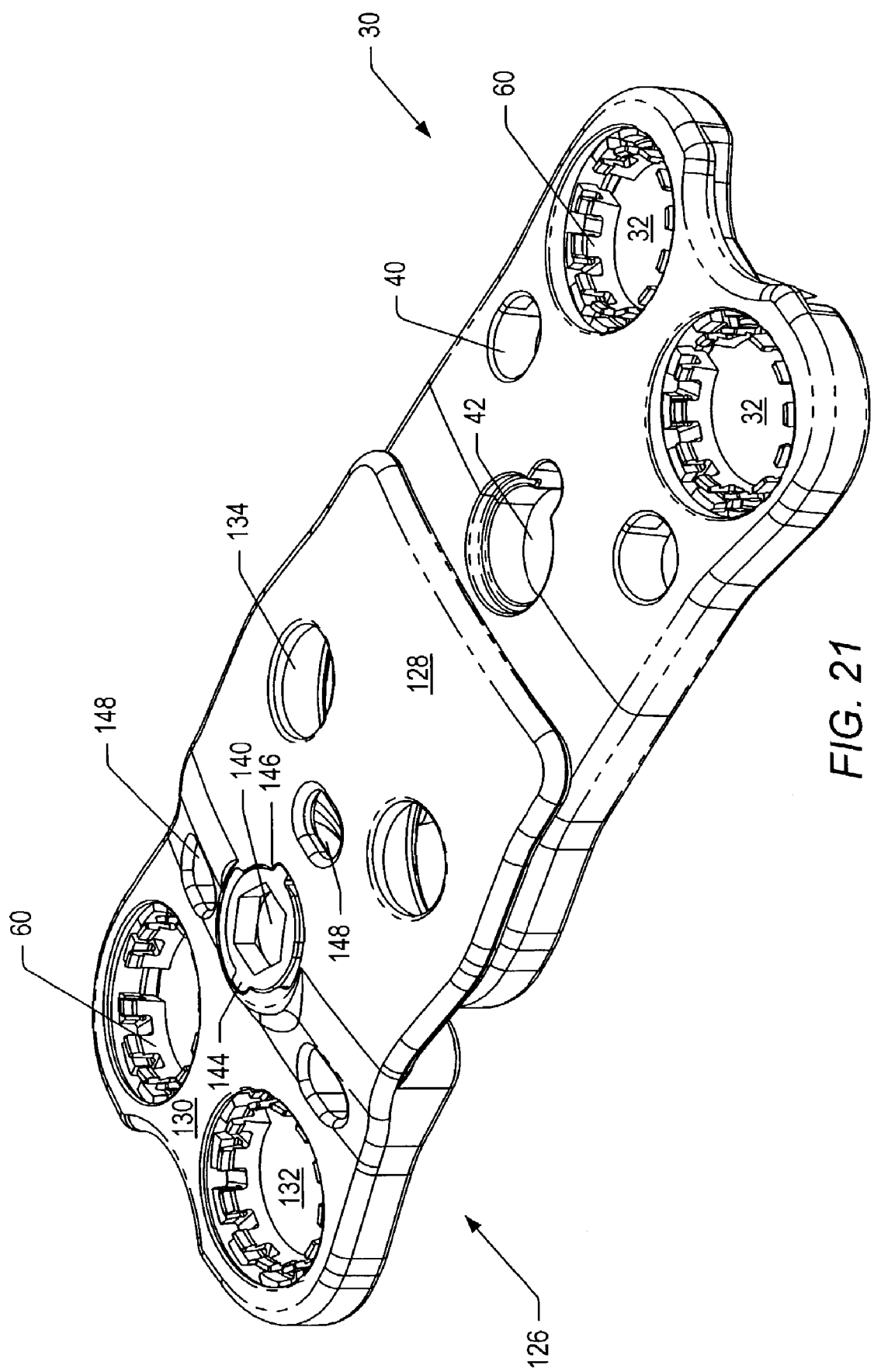
FIG. 21 depicts a perspective view of an embodiment of an extender plate coupled to an embodiment of a base plate.

Extender plate 126 may include an engagement mechanism. The engagement mechanism may include head 140 (shown in FIG. 19), and cam 142 (shown in FIG. 20). Head 140 may be located on a top surface of extender plate 126. Head 140 may include a tool opening and an arm or arms 144. The tool opening may accept a drive tool (e.g., a hex driver) that is able to rotate head 140. Rotating head 140 changes the position of cam 142. Orientation of arms 144 may indicate if cam 142 is an engaged or non-engaged position. When head 140 is in a first position as depicted in FIG. 19, cam 142 is in a non-engaged position. When head 140 is rotated about 90°, cam 142 extends to an engaged position. FIG. 21 depicts position of head 140 when cam 142 is in an engaged position. Arms 144 may engage stops 146 to indicate to a user when cam 142 is in the engaged position. When cam 142 is in the engaged position, the cam may fit under ledge 46 of base plate 30 (shown in FIG. 2) and press against the base plate. Contact of cam 142 against the base plate may move tabs 136 of extender plate 126 fully into extender plate mounts of the base plate. Full insertion of tabs 136 into the extender plate mounts and contact of cam 142 against the base plate may inhibit movement of extender plate 126 relative to the base plate.

Figure 22:
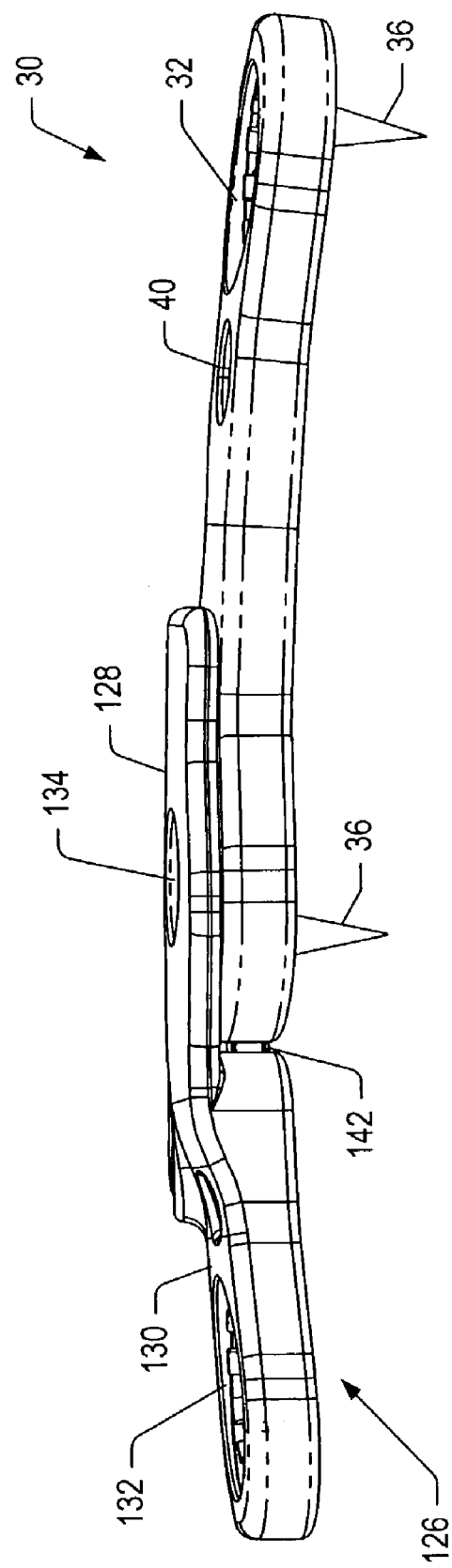
FIG. 22 depicts a side view of an embodiment of an extender plate coupled to an embodiment of a base plate.
Figure 23:
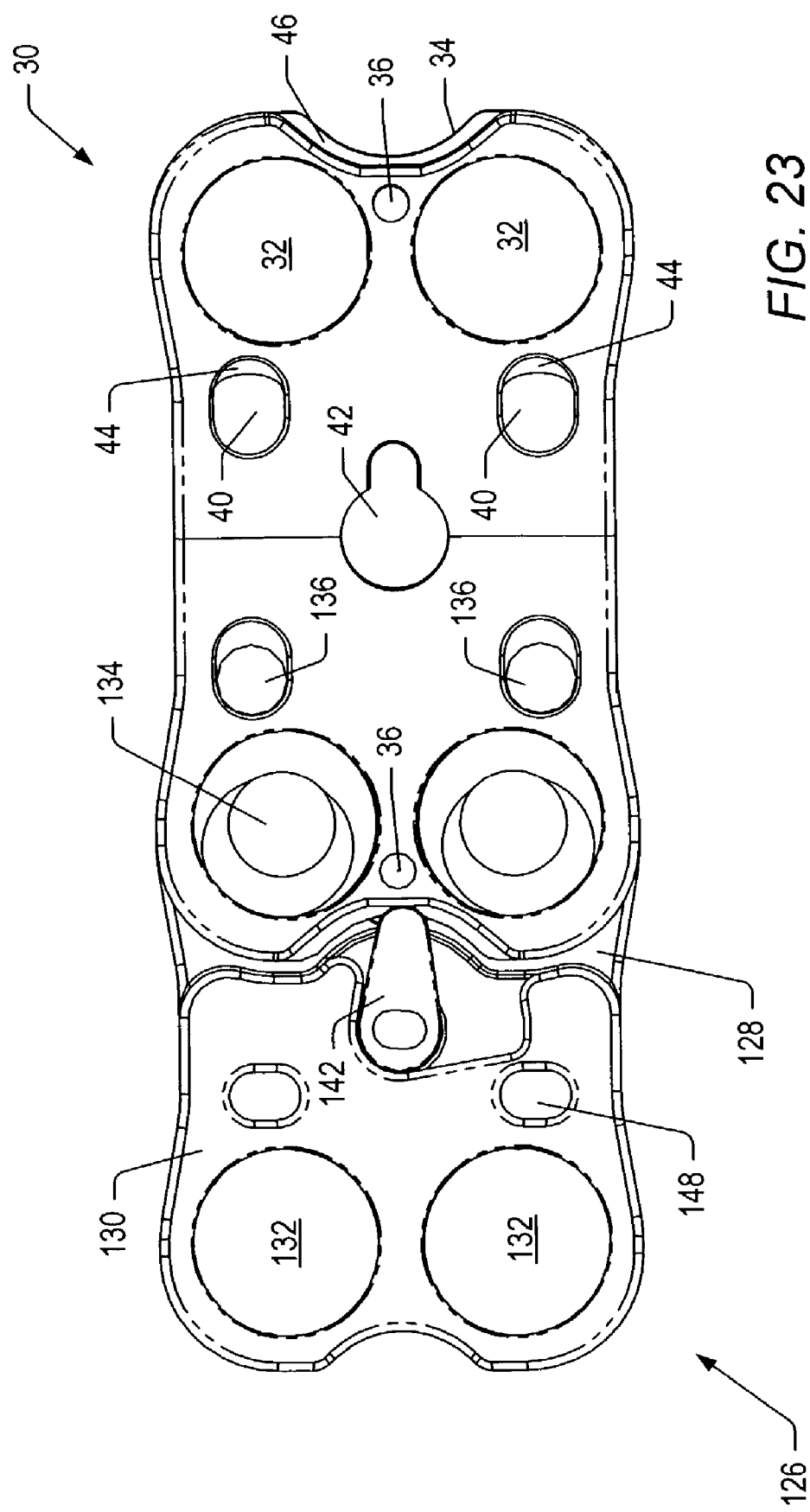
FIG. 23 depicts a bottom view of an embodiment of an extender plate coupled to an embodiment of a base plate.

FIG. 21, FIG. 22, and FIG. 23 depict embodiments of extender plates that are coupled to embodiments of base plates 30. Extender plate 126 may include openings 148, as shown in FIG. 21. During installation of extender plate 126, an anti-torquing wrench may be positioned in openings 148. The anti-torquing wrench may be used to inhibit application of torque to extender plate 126 and to base plate 30 when head 140 is rotated to move a cam against the base plate.

FIG. 22 depicts a side view of base plate 30 that is coupled to extender plate 126. Overlay section 128 is positioned on extender plate 126 to overlay at least a portion of base plate 30. In some embodiments, openings 134 in overlay section 128 may be positioned over fasteners in openings in base plate 30. In some embodiments, coupling section 130 may have a thickness that is similar to a thickness of base plate 30. In some embodiments, coupling section 130 may include a curvature similar to a curvature of base plate 30. In some embodiments, coupling section 130 may include a different curvature. When positioned on an adjacent vertebra or vertebrae, extender plate 126 may provide desired lordotic alignment to the adjacent vertebrae.

FIG. 23 depicts a bottom view of extender plate 126 coupled to base plate 30. Cam 142 may be positioned in a locked orientation as shown by rotating a head of an engagement mechanism. When cam 142 is in a locked orientation, the cam pushes against base plate 30. A portion of cam 142 may contact ledge 46 in indention 34. The locked orientation may inhibit removal of extender plate 126 from base plate 30.

A base plate may be coupled to a spine during a spinal fusion procedure. The base plate may be installed using an anterior approach. Fasteners may be inserted into vertebrae to couple the base plate to the vertebrae. In many applications, fusion of the spine will occur and no further action will be required. In some applications, stabilization of an adjacent vertebra or vertebrae may be required after a period of time has elapsed. An extender plate may be coupled to the base plate to provide stabilization of a vertebra or vertebrae adjacent to the installed base plate.

An anterior approach may be used to install an extender plate. Fasteners that couple the base plate to a vertebra on the side to which the extender plate is to be attached may be loosened. Loosening the fasteners may provide space between the vertebra and the base plate to allow for easy attachment and positioning of extender plate tabs in the extender plate mounts of the base plate. After positioning of extender plate tabs in extender plate mounts, the engagement mechanism of the extender plate may be activated by rotating the head to move the cam. An anti-torquing wrench may be coupled to the extender plate to inhibit rotation of the extender plate and base plate when the head is rotated. The cam may contact the base plate and fix the extender plate to the base plate. Openings may be drilled and/or tapped in the vertebra beneath fastener openings in the extender plate. Fasteners may be inserted into the fastener openings to couple the extender plate to the vertebra.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for stabilizing at least three vertebrae in a spine, comprising:
    attaching a base plate to a first vertebra by positioning a first bone fastener through a first opening in the base plate;
    attaching the base plate to a second vertebra by positioning a second bone fastener through a second opening in the base plate;
    coupling an extender plate to the base plate after the base plate is attached to the first vertebra and the second vertebra wherein the step of coupling the extender plate to the base plate comprises positioning a portion of the extender plate over a non-bone contacting top surface of the base plate;
    loosening the second bone fastener to enable coupling the extender plate to the base plate;
    attaching the extender plate to a third vertebra by positioning a third bone fastener through an opening in the extender plate,
    wherein the extender plate is attached to the third vertebra after the base plate is attached to the first vertebra and the second vertebra,
    wherein the first vertebra is adjacent to the second vertebra, and
    wherein the third vertebra is adjacent to the second vertebra.

2. The method of claim 1, wherein the step of coupling the extender plate to the base plate comprises attaching the extender plate to mounts on the base plate.

3. The method of claim 1, wherein the step of coupling the extender plate to the base plate comprises using a coupling device.

4. The method of claim 3, wherein the coupling device is a protruding member, recess, or opening on the base plate that receives tabs, protruding members, or engagers from the extender plate.

5. The method of claim 1, wherein the extender plate is coupled to the base plate after degeneration of an adjacent intervertebral disc occurs.

6. The method of claim 1, wherein the step of coupling the extender plate to the base plate comprises activating an engagement mechanism on the extender plate, and
wherein when the extender plate is coupled to the base plate, the engagement mechanism contacts the base plate to inhibit movement of the extender plate relative to the base plate.

7. The method of claim 6, wherein the step of activating the engagement mechanism comprises rotating a cam.

8. The method of claim 1, wherein the first bone fastener is a bone screw.

9. The method of claim 1, wherein the step of attaching the base plate to the first vertebra comprises positioning two bone fasteners through two openings in the base plate.

10. The method of claim 1, wherein the extender plate comprises a protruding member,
wherein the base plate comprises a cavity, and
wherein the step of coupling the extender plate to the base plate comprises engaging the cavity with the protruding member.

11. The method of claim 1, wherein the extender plate comprises a movable member,
wherein the base plate comprises a cut-out, and
wherein the step of coupling the extender plate to the base plate comprises engaging the cut-out with the movable member.

12. The method of claim 1, wherein the step of coupling the extender plate to the base plate comprises moving a cam lock to engage a cut-out on the underside of the base plate.

13. A method for stabilizing a vertebra following degeneration of an adjacent intervertebral disc following a first fusion procedure, comprising the steps of:
coupling an extender plate to a base plate by positioning a portion of the extender plate over a non-bone contacting top surface of the base plate, said base plate having been installed during a first fusion procedure to fuse a first vertebra and a second vertebra;
loosening a second bone fastener to enable coupling of the extender plate to the base plate, wherein the second bone fastener secures the base plate to the second vertebra; and
attaching the extender plate to a third vertebra by positioning a bone fastener through an opening in the extender plate,
wherein the first vertebra is adjacent to the second vertebra, and
wherein the third vertebra is adjacent to the second vertebra.

14. The method of claim 13, wherein the extender plate comprises a protruding member,
wherein the base plate comprises a cavity, and
wherein the step of coupling the extender plate to the base plate comprises engaging the cavity with the protruding member.

15. A method for stabilizing a vertebra following degeneration of an adjacent intervertebral disc following a first fusion procedure, comprising the steps of:
loosening a first bone fastener, said first bone fastener installed during a first fusion procedure to secure a base plate to a second vertebra;
coupling an extender plate to the base plate after the first bone fastener is loosened by positioning a portion of the extender plate over a non-bone contacting top surface of the base plate; and
attaching the extender plate to a third vertebra by positioning a second bone fastener through an opening in the extender plate,
wherein the first vertebra is adjacent to the second vertebra, and
wherein the third vertebra is adjacent to the second vertebra.

16. The method of claim 15, wherein the extender plate comprises a protruding member,
wherein the base plate comprises a cavity, and
wherein the step of coupling the extender plate to the base plate comprises engaging the cavity with the protruding member.

* * * * *